(12) United States Patent
Sekitani et al.

(10) Patent No.: US 11,509,123 B2
(45) Date of Patent: Nov. 22, 2022

(54) WIRING SHEET, SHEET-SHAPED SYSTEM, AND STRUCTURE OPERATION SUPPORT SYSTEM

(71) Applicant: OSAKA UNIVERSITY, Osaka (JP)

(72) Inventors: Tsuyoshi Sekitani, Osaka (JP); Takafumi Uemura, Osaka (JP); Shusuke Yoshimoto, Osaka (JP); Teppei Araki, Osaka (JP); Yuki Noda, Osaka (JP); Takayasu Sakurai, Tokyo (JP); Tokihiko Mori, Tokyo (JP); Makoto Takamiya, Tokyo (JP)

(73) Assignee: OSAKA UNIVERSITY, Osaka (JP)

( * ) Notice: Subject to any disclaimer, the term of this patent is extended or adjusted under 35 U.S.C. 154(b) by 619 days.

(21) Appl. No.: 16/319,694

(22) PCT Filed: Jul. 25, 2017

(86) PCT No.: PCT/JP2017/026876
§ 371 (c)(1),
(2) Date: Jan. 22, 2019

(87) PCT Pub. No.: WO2018/021315
PCT Pub. Date: Feb. 1, 2018

(65) Prior Publication Data
US 2021/0328417 A1    Oct. 21, 2021

(30) Foreign Application Priority Data

Jul. 25, 2016  (JP) .............................. JP2016-145777
Jul. 21, 2017  (JP) .............................. JP2017-142222

(51) Int. Cl.
*H02G 3/30* (2006.01)
*G01M 5/00* (2006.01)
(Continued)

(52) U.S. Cl.
CPC ............ *H02G 3/30* (2013.01); *G01M 5/0033* (2013.01); *G01N 33/383* (2013.01); *H05K 1/09* (2013.01);
(Continued)

(58) Field of Classification Search
CPC ....................................................... H02G 3/30
(Continued)

(56) References Cited

U.S. PATENT DOCUMENTS 3,763,306 A    10/1973  Marshall
5,281,765 A *  1/1994  Iura ...................... H01B 7/0838
                                                        174/117 F
(Continued)

FOREIGN PATENT DOCUMENTS

CN         1115485         1/1996
CN        102099531        6/2011
(Continued)

OTHER PUBLICATIONS

Extended European Search Report dated Feb. 7, 2020 in corresponding European Patent Application No. 17834317.4.
(Continued)

*Primary Examiner* — Stanley Tso
(74) *Attorney, Agent, or Firm* — Wenderoth, Lind & Ponack, L.L.P.

(57) ABSTRACT

A wiring sheet includes one or more carbon wires each of which is one of a signal line and a power supply line, and which are conductors including carbon as a main material and have flexibility; and an insulation sheet that encloses substantially an entirety of the one or more carbon wires, includes an electrical insulator as a main material, and has flexibility.

12 Claims, 10 Drawing Sheets

(51) Int. Cl.
  *G01N 33/38* (2006.01)
  *H05K 1/09* (2006.01)
(52) U.S. Cl.
  CPC ............... *H05K 2201/0323* (2013.01); *H05K 2201/10151* (2013.01)
(58) Field of Classification Search
  USPC ........................................................ 361/700
  See application file for complete search history.

(56) References Cited

U.S. PATENT DOCUMENTS

| | | | | |
|---|---|---|---|---|
| 5,847,572 | A * | 12/1998 | Iwasaki | G01R 1/0433 324/754.08 |
| 6,042,894 | A | 3/2000 | Goto et al. | |
| 8,075,181 | B1 * | 12/2011 | Stauffer | G01K 1/026 374/137 |
| 9,437,372 | B1 * | 9/2016 | Zhamu | C04B 35/52 |
| 2004/0262765 | A1 * | 12/2004 | Burton | H01L 23/5222 257/758 |
| 2011/0187394 | A1 * | 8/2011 | Rodel | E02D 31/02 324/699 |
| 2012/0253162 | A1 * | 10/2012 | Jones | A61N 1/0472 600/382 |
| 2013/0251619 | A1 | 9/2013 | Rikihisa et al. | |
| 2014/0292103 | A1 | 10/2014 | Waffenschmidt et al. | |

FOREIGN PATENT DOCUMENTS

| | | |
|---|---|---|
| CN | 102604387 | 4/2014 |
| EP | 2 226 618 | 9/2010 |
| JP | 4-29840 | 5/1992 |
| JP | 05-048124 U | 6/1993 |
| JP | 8-193993 | 7/1996 |
| JP | 2003-016848 A | 1/2003 |
| JP | 2013-13 9697 | 7/2013 |
| JP | 2013-139697 | 7/2013 |
| JP | 2014-526233 | 10/2014 |
| WO | 2012/070537 | 5/2012 |
| WO | 2013/024417 | 2/2013 |

OTHER PUBLICATIONS

Office Action dated Sep. 2, 2020 issued for the corresponding European Patent Application No. 17834317.4.
Office Action with Search Report dated Oct. 11, 2019 in corresponding Chinese Patent Application No. 201780045642.5.
Communication pursuant to Article 94(3) EPC dated Apr. 1, 2021 in corresponding European Patent Application No. 17834317.4.
International Search Report (ISR) dated Aug. 29, 2017 in International (PCT) Application No. PCT/JP2017/026876.

* cited by examiner

WIRING SHEET, SHEET-SHAPED SYSTEM, AND STRUCTURE OPERATION SUPPORT SYSTEM

TECHNICAL FIELD

The present invention relates to a wiring sheet that is a sheet body including a conductive line, and a system that includes the wiring sheet.

BACKGROUND ART

For bringing efficiency to maintenance operation of structures and prolonging cycles of repairing the structures, which have been conducted by human power at different sites, various ideas have been produced.

For example, in a concrete-made structure such as a tunnel, a crack may occur on a wall surface of concrete with lapse of time after its completion. In an environment where rainwater, groundwater, or the like enters this crack, the water may freeze in winter, further widening the crack. Such a crack can cause flaking off of the wall surface, posing danger. To prevent such danger, measures for preventing freezing by disposing conductive lines on a wall surface at a time of repairing a crack on the wall surface and energizing these conductive lines from a wiring for illumination to emit heat are proposed (see Patent Literature (PTL) 1).

In conventional practices, checking for an anomaly in a concrete-made structure such as a crack is performed by hammering diagnosis or the like conducted by human power at the site; however, there are technical proposes relating to a device and the like that replace such manual inspection operations. For example, a technique for inspecting a structure by analyzing captured images obtained by a camera fixed at a stationary point or mounted on a traveling vehicle is proposed.

CITATION LIST

Patent Literature

[PTL 1] Japanese Examined Patent Application Publication No. H04-029840.

SUMMARY OF INVENTION

Technical Problem

Nowadays, the development of a society expressed as "Internet of Things (IoT)" is advancing, and there is an idea that sensors are directly attached to a structure as described above, and information on a status of the structure is remotely collected from these sensors. If the information from the sensors can be remotely acquired through communication, it is possible to acquire information on the state of the structure at a frequency higher than that of a case where an inspection engineer is dispatched to the site, or at any time as necessary.

In a concrete-made structure, a proportion of parts reaching their useful lives to the entire facility is increasing, and in such circumstances, performing manual inspections at a frequency necessary to ensure its safety is expected to lead to a high cost. Thus, by using sensors as described above, it is possible to perform measurement and obtain physical quantities that cannot be obtained from images, and to diagnose a state of the structure.

However, to realize the collection of information using sensors installed in a structure, there are problems described below.

First, a structure having a demand for inspection using such sensors may be a harsh environment for wirings for power supply to the sensors and for communication with the sensors. For example, an environment where concrete easily deteriorates and therefore a highly-reliable inspection is required at a relatively high occurrence can be an environment that contains a large amount of chloride or an environment having a high acidity, where metallic wirings commonly used to power supply and communication also easily deteriorate. Therefore, to install wirings that are reliable for a long term, securing a redundancy and a cost of continuous maintenance are needed.

In addition, structures that need inspections, particularly, infrastructures for traffic, communication, and the like are often very large-scale; for example, a total distance of tunnels for communication lines (service tunnels) in a telecommunications company is said to reach 600 km. In addition, a total distance of service tunnels for power transmission lines that an electric power company possesses in its service area reaches 2000 km or longer. Structures of such scales allow persons to enter but are relatively narrow and have complex shapes with many curved surfaces.

That is, using sensors directly attached to a structure, it is possible to perform periodic inspections of such a service tunnel reliably, more quickly, and easily. However, building an inspection system that includes a large number of sensors necessary for monitoring such a large-scale structure with complex shapes involves a problem in that it is difficult to establish compatibility between ensuring a long-term reliability in a harsh environment and reducing a cost.

The present invention is conceived in view of such problems and has an object to provide a wiring sheet that can widely support a shape and an environment of a location where the wiring sheet is installed and reduces initial cost and running cost, and provides a sheet-shaped system including the wiring sheet, and the like.

Solution to Problem

In order to achieve the aforementioned object, a wiring sheet according to an aspect of the present invention includes: one or more carbon wires that are conductors including carbon as a main material and have flexibility, each of the one or more carbon wires being one of a signal line and a power supply line; and an insulation sheet that encloses substantially an entirety of the one or more carbon wires, includes an electrical insulator as a main material, and has flexibility.

This enables a wiring having a high resistance to environment to be installed along a surface of a structure.

Furthermore, the main material of the one or more carbon wires may be any one of graphene, graphite, and carbon nanotube, and the main material of the insulation sheet may be any one of resin, cloth, and paper.

This enables a wiring that has a high resistance to environment and can be used for a long term while meeting various demands for appearance of installation locations to be installed, in a form of a sheet including a wiring. In addition, the material of the carbon wires can be selected in consideration of a cost and a required performance (resistance).

Moreover, for example, the main material of the insulation sheet may be polyvinyl chloride resin.

Polyvinyl chloride resin provides a flexibility that enables complex shapes. In addition, polyvinyl chloride resin has a resistance in an environment that has high humidity and can contain salt, such as an inside of a service tunnel. Nevertheless, polyvinyl chloride resin can be secured at relatively low cost; it is therefore possible to, for example, reduce a cost to introduce the wiring sheet installed in a service tunnel and a running cost occurring thereafter.

Furthermore, the one or more carbon wires may include a carbon wire that has a resistance per centimeter of at least 0.01 ohms and at most 1 ohm.

Furthermore, the one or more carbon wires may include the power supply line, and the power supply line may form a grid.

An electrical pathway in a two-dimensional shape thereby provided has a resistance lower than that of a pathway in a one-dimensional shape using one linear carbon wire, enabling power to be conveyed more efficiently. In addition, on a wiring sheet that encloses such carbon wires and extends two-dimensionally, a spot to take power can be selected with a high degree of freedom. Such a configuration of a wiring sheet is applicable to, for example, wallpaper or the like. When a wall surface of a room or the like is covered with this wallpaper, and the carbon wire is connected to a power source, it is possible to take power at different spots on the wall surface. In addition, such wallpaper allows for providing spots to attach a load including an electric circuit across a wide area without large-scale work, making it easy to introduce an IoT technology.

Furthermore, the insulation sheet may include a via for connecting a conductor outside the insulation sheet and the carbon wires.

This can provide a system in which a plurality of loads connected to a wiring having a high resistance can be disposed along a surface of a structure.

Furthermore, the insulation sheet may include a contact that includes anisotropic conductive rubber, be capable of being conductive in a thickness direction of the insulation sheet, and be configured to electrically connect a conductor outside the insulation sheet and the carbon wires.

It is thereby possible to electrically connect, for example, the terminals of the above loads installed on an insulation sheet or a wiring for electrical connection with these terminals to carbon wires enclosed in the insulation sheet, more reliably. In addition, it is possible to insulate the carbon wires inside the insulation sheet as with spots covered by the insulation sheet when no load is connected.

Furthermore, the one or more carbon wires may include three or more carbon wires, and the three or more carbon wires may include the power supply line, the signal line, and a first GND line.

In a location where this wiring sheet is installed, it is possible to dispose loads that receive a supply of power from a power supply line having a high resistance to environment and output signals to a signal line having a high resistance to environment.

Furthermore, in the insulation sheet, the power supply line, the signal line, and the first GND line may extend in parallel to each other, and the signal line may be positioned between the power supply line and the first GND line.

A long signal line may act as an antenna under an influence of carried signals and may emit radio waves, and the radio waves may be a cause of radio interference such as causing another signal line lying around the long signal line to produce noise and causing a misoperation or the like of an electronic device. The above configuration reduces harmonic components contained in a signal in the signal line that cause the radio interference, through a capacity coupling between the signal line and the power supply line and a capacity coupling between the signal line and the first GND line.

Furthermore, a sheet-shaped system according to an aspect of the present invention includes: any one of the above described wiring sheets; and a plurality of loads that are electrically connected to the one or more carbon wires from an outside of the insulation sheet. The one or more carbon wires include the power supply line. The plurality of loads each include: a power storage element configured to receive and store a supply of power from the power supply line; and an electric circuit configured to receive a supply of power from the power storage element to operate intermittently.

This enables a system in which, for example, loads operates at regular times as the intermittent operation to be provided using power supply lines that have a relatively high resistance but are less expensive. In this system, the power storage elements can be charged using supplied power at times when the loads operates at regular times. That is, the charging of the power storage elements can be performed with a limited current. It is therefore possible to reduce a resistance loss.

Furthermore, the one or more carbon wires may include the signal line, and the electric circuit may include a sensor and is configured to output, via the signal line, a physical quantity measured by the sensor.

This can provide a sheet-shaped system including sensors that receive power from power supply lines capable of enduring an environment such as a service tunnel and output signal indicating results of measurements to signal lines capable of enduring the same environment.

Furthermore, the one or more carbon wires may include two or more carbon wires, and the two or more carbon wires may include a second GND line through which substantially no current flows and is used to establish a grounding potential.

This can provide a sheet-shaped system that can, for example, measure surface potentials of a structure as an installation location more accurately.

Furthermore, the one or more carbon wires may include the power supply line, and the plurality of loads may each include an electric circuit configured to return power stored in the power storage element to the power supply line.

In the above sheet-shaped system, poor charging may occur in some loads under an influence a voltage drop occurring due to a relatively large resistance of the power supply line. However, the above configuration allows neighboring loads that share the power supply line in the sheet-shaped system to interchange their power when possible. This can enhance stability of the operation of the sheet-shaped system as a whole.

Furthermore, the one or more carbon wires may include the power supply line, the sheet-shaped system may comprise a gateway that electrically connects an electrical wire through which electricity from a power source outside of the sheet-shaped system flows to the power supply line, and the gateway may be configured to give instructions on whether to receive a supply of power from the power source via the power supply line, to the plurality of loads.

With this, for example, the voltage drop is suppressed by limiting the number of loads that are charged simultaneously, and charging is thereby normally performed on the loads of the sheet-shaped system.

Furthermore, a structure operation support system according to an aspect of the present invention includes: a plurality of sheet-shaped systems each of which is the sheet-shaped system according to any one of claims 10 to 14 that are configured to be installed on a surface of a structure; and an electrical wire to which the one or more carbon wires included in each of the plurality of sheet-shaped systems are connected.

This can provide a structure operation support system that can include a plurality of sheet-shaped systems capable of being installed in conformity to a shape of a surface of a structure being an installation surface according to a scale of the structure and allows a long-term, stable operation of loads on each sheet-shaped system.

Advantageous Effects of Invention

The present invention provides a wiring sheet that can widely support a shape and an environment of a location where the wiring sheet is installed and reduces an initial cost and a running cost, and provides a sheet-shaped system including the wiring sheet.

DESCRIPTION OF EMBODIMENTS

Embodiment

Figure 1:
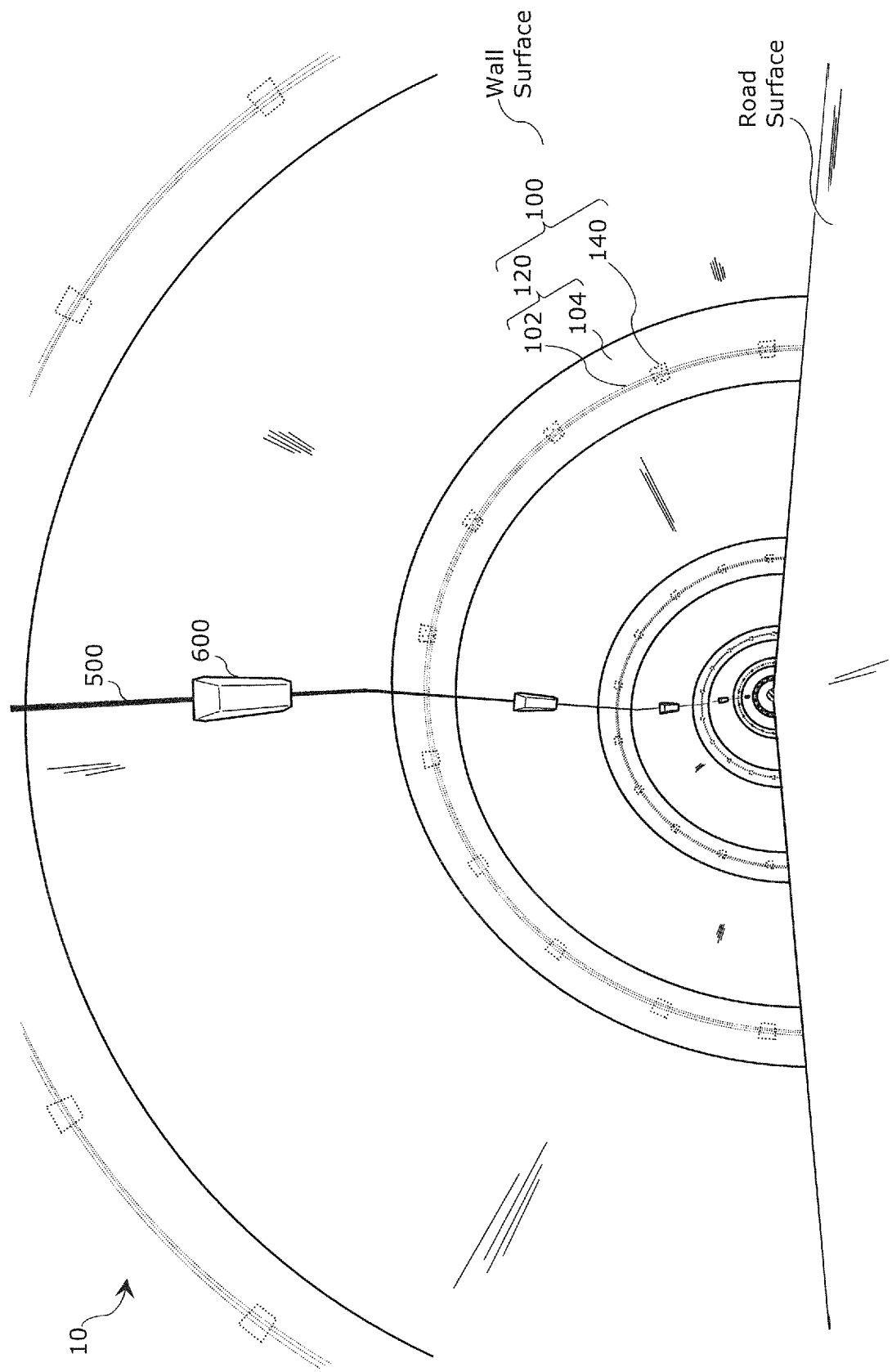
FIG. 1 is a diagram illustrating an installation example of a structure operation support system that is provided using wiring sheets according to an embodiment.

Hereafter, an embodiment will be described in detail with reference to the drawings.

Note that each embodiment described below shows a general or specific example of the present invention. Numeric values, shapes, materials, constituent components, disposition and connection of the constituent components, and the like shown in the following embodiment are mere examples and are not intended to restrict the scope of the present invention. In addition, of the constituent components in the following embodiment, constituent components not recited in the independent claims each indicating the top concept are described as optional constituent components.

In addition, the drawings referred to in the following description are schematic diagrams and do not show shapes and sizes of the constituent components exactly. In the drawings, common constituting members will be denoted by the same reference characters.

[1. Configuration]
[1-1. Outline]

Figure 2:
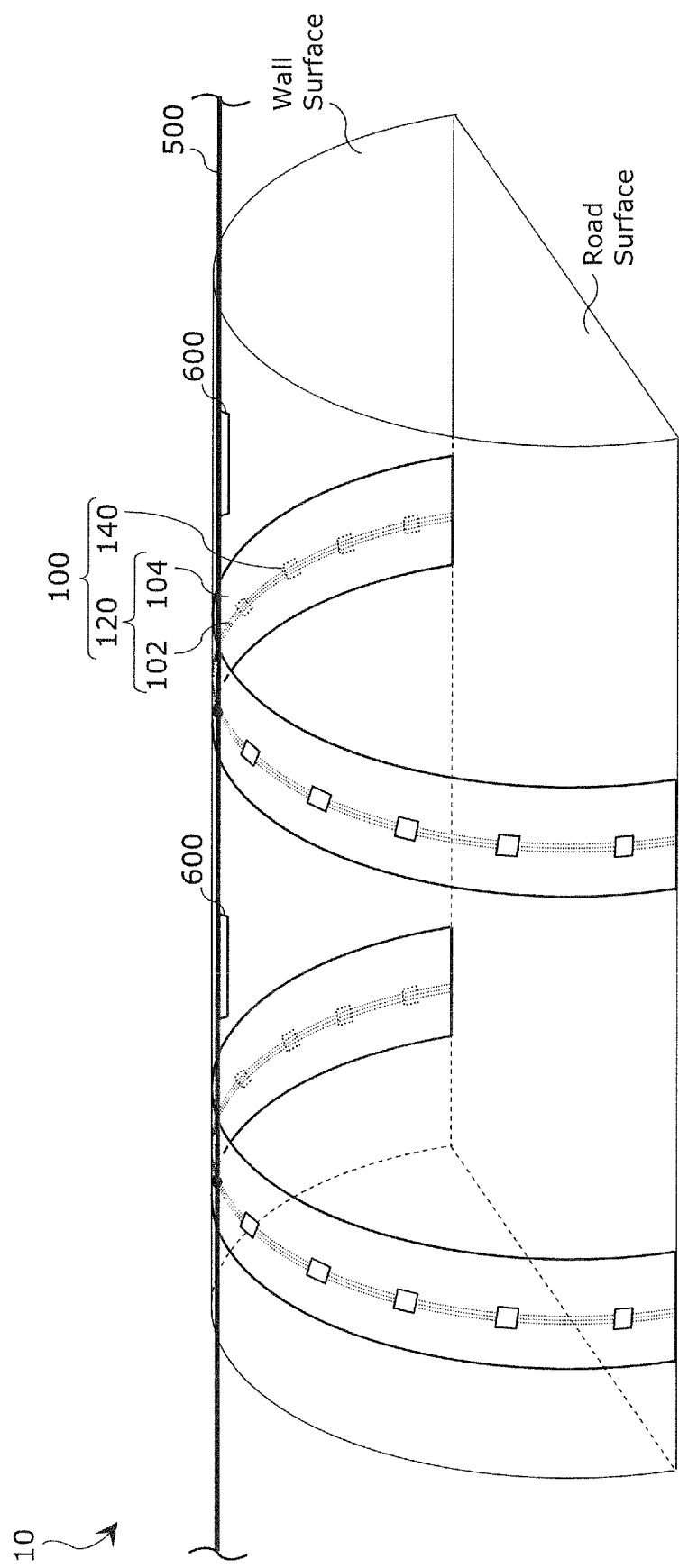
FIG. 2 is a schematic diagram illustrating how the above structure operation support system is seen in perspective from outside of a structure.

FIG. 1 is a diagram illustrating an installation example of a structure operation support system that is provided using wiring sheets according to the present embodiment. This drawing illustrates how a structure operation support system 10 is installed on a wall surface of a structure. FIG. 2 is a schematic diagram illustrating how the structure operation support system 10 illustrated in FIG. 1 is seen in perspective from outside of the structure.

The structure illustrated in these drawings is, for example, a service tunnel that extends underground with a wall surface including a concrete material and a road surface. The service tunnel is substantially in a circular-tube shape with a size that at least allows a person to pass therethrough walking on a road surface therein, and an arch-shaped wall surface in FIG. 1 is an inner surface of this circular-tube shape. The road surface is a surface that is provided on a lower side in the circular tube and on which passers walk.

Note that the drawing illustrates how an inside of the service tunnel is in a simplified manner for description, and in actuality, such a service tunnel includes communication lines where it belongs to a telecommunications company, or power transmission lines where it belongs to a power company, racks supporting these lines, and lighting fixtures and communication lines for workers, and the like. The wall of the service tunnel is partially behind such power transmission lines and the like. Inspection of such a service tunnel in conventional practices is conducted by, for example, an inspection engineer hearing hammering sound made by hammering the wall surface with a diagnosis hammer. That is, even an inspection conducted by a human hearing hammering sound cannot be always done on the entire wall surface easily.

The structure operation support system 10 includes a plurality of sheet-shaped systems 100 and an electrical wire 500 that connects the sheet-shaped systems 100.

The sheet-shaped systems 100, each of which is installed in such a manner as to extend along a circumferential direction in the wall surface of the service tunnel, each include a wiring sheet 120 and a plurality of loads 140. The wiring sheet 120 measures, for example, about 10 m in its long-side direction. A distance between the loads 140 on the wiring sheet 120 is, for example, about 1 m. A distance between the wiring sheets 120 is, for example, about 10 m.

The wiring sheet 120 includes carbon wires 102 and an insulation sheet 104. In the example illustrated in FIG. 1 and FIG. 2, the wiring sheets 120 each include three carbon wires 102, which are illustrated by dotted lines. The wiring sheet 120 covers substantially the entirety of the carbon wires 102, and the carbon wires 102 are basically not exposed to the outside of the wiring sheet 120 except a portion necessary for connection to the outside. FIG. 1 and FIG. 2 however illustrate the presence and disposition of the carbon wires 102, which are invisible from the outside, with the dotted lines for the sake of convenience.

In the structure operation support system 10, the carbon wires 102 are each used as a signal line or a power source line. In the description of the present embodiment, the term "power source line" is used as a term that can refer both to a power supply line and a combination of a power supply line and a GND (GROUND) line. The GND line used in combination with the power supply line that forms a conception of the power source line will be also referred to as a first GND line in the present specification and the like.

The carbon wires 102 are lines that are conductors including carbon as a main material and have flexibility. More specific examples of the material include graphene, graphite, and single-layer or multilayer carbon nanotube.

One of reasons for using these as a main material is that carbon has a property of resisting ionizing, that is, corroding. As such, the carbon wires 102 including these materials are provided as wires that preserve their structures and electric properties even in an environment such as one under ground where the water content is high, an environment where soil has a high acidity or alkalinity, or an environment such as a coast region where a chloride-ion content is high. These materials are controllable in their initial cost because they are expected to be provided more stably than copper, which are often used in wiring for power supply or communications. In addition, it is relatively easy for these materials to be produced or worked for application of the materials to large structures, these materials impose a small workload because they are relatively lightweight, and they are less likely to impose a load on a structure after installation, which are also reasons for using the materials.

Carbon wires 102 including these materials show different specific resistances. Specifically, a carbon wire 102 including graphite has a specific resistance higher than that of a carbon wire 102 including single-layer carbon nanotube, and a carbon wire 102 including graphene or multilayer carbon nanotube has a specific resistance therebetween. On the other hand, graphite has the lowest price of them, multilayer carbon nanotube has the highest price, and graphene and multilayer carbon nanotube had a price therebetween. One of these materials to be used therefore can be selected as appropriate in consideration to, for example, an initial cost, power consumption of the loads 140, and the like. The material of the carbon wires 102 may contain substances other than carbon; for example, carbon wires 102 having lower specific resistances are obtained by using these materials doped with boron. The material can contain binder as necessary.

A shape and size of each carbon wire 102 are determined in consideration of the resistance and the flexibility. That is, the carbon wires 102 each need to have a cross-sectional area large enough not to make their resistances excessively high for power supply and signal transmission. Meanwhile, the carbon wires 102 each need to be slender or thin enough to allow the carbon wires 102 to be deformed into shapes extending along structures. Examples of a shape of each carbon wire 102 satisfying the above include a string shape or a ribbon shape. For example, a carbon wire 102 including single-layer carbon nanotube can be made to have a resistance per centimeter of about 0.01 ohms. A carbon wire 102 including graphite can be made to have a resistance per centimeter of about 1 ohm. Use of carbon wires 102 having such resistances as signal lines or power source lines enables the structure operation support system 10 in the present embodiment to be operated practically.

The insulation sheets 104 cover the carbon wires 102 as described above to protect the carbon wires 102 against a physical impact to some extent and make the carbon wires 102 easy to handle.

The insulation sheets 104 include an electrical insulator as a main material. With this insulation property, the insulation sheets 104 protect the carbon wires 102 that act a role of a power source line or a signal line against an electrical influence from the outside. In addition, the insulation sheets 104 each fix the carbon wires 102 in a positional relationship in which the enclosed carbon wires 102 do not come into contact with each other unnecessarily, preventing an effect caused by the carbon wires 102 coming into contact with each other. Disposition and the like of a plurality of carbon wires 102 in an insulation sheet 104 will be described later.

The insulation sheets 104 have flexibility. With this property, the insulation sheets 104 are each enabled to be attached to a structure having a curved surface or a curved portion as illustrated in FIG. 1 and FIG. 2 in such a manner as to fit a shape of a surface of the structure.

Examples of an insulation sheet 104 having such properties include organic macromolecules such as resins.

Of the resins, for example, polyvinyl chloride resin is impervious to water and excellent in acid resistance and alkaline resistance. In addition, by adjusting an amount of plasticizer to be added in production of polyvinyl chloride resin, it is possible to impart flexibility to the polyvinyl chloride resin. The polyvinyl chloride resin having such properties is formed into a flexible sheet and used in conventional practices as a sheet that covers seams on a wall surface of a service tunnel to prevent groundwater from entering the service tunnel. Such a sheet including the polyvinyl chloride resin is said to have an approximate-70-year endurance when installed in an environment where the sheet will not be exposed to heat over 60° C. or ultraviolet rays. Insulation sheets 104 including such polyvinyl chloride resin as a main material can protect carbon wires 102 enclosed therein against moisture, chloride ions, acid or alkaline substances present in a surrounding environment for a period as long as several tens of years in a service tunnel that shields sunlight and a temperature of which allows a worker to perform operation without wearing a heat-resistant suit. The wiring sheets 120 including such insulation sheets 104 allow frequent replacement to be dispensed with, reducing a maintenance cost of the structure operation support system 10.

Moreover, polyvinyl chloride resin is relatively less expensive than other kinds of resins. The installation and replacement of the waterproof polyvinyl chloride resin sheets described above on a wall surface of a service tunnel is operations that have been conducted and are also originally planned from now on. By replacing waterproof sheets with wiring sheets 120 from now on, it is possible to reduce an initial cost of the structure operation support system 10 to a large-scale structure such as a service tunnel.

The number of kinds of materials for forming one insulation sheet 104 is not limited to one. For example, an insulation sheet 104 may be formed of a plurality of layers including different materials. A structure of one insulation sheet 104 may be uniform as a whole or may be nonuniform portion to portion. Being nonuniform portion to portion may refer to, for example, an insulation sheet 104 may have a multilayered structure at positions of attaching loads to reinforce or fix the loads 140 and have a single-layer structure in the rest of the installation sheet 104.

The plurality of loads 140 are disposed on a surface of such a wiring sheet 120 spaced at a predetermined distance along the carbon wires 102. In the example illustrated in FIG. 1 and FIG. 2, 10 loads 140 are disposed about 1 m apart on a surface of the wiring sheets 120 on a side being in contact with the wall surface of the service tunnel.

The loads 140 in the present embodiment each include an electric circuit with a sensor, and the electric circuit is connected to the carbon wires 102 through vias included in the insulation sheet 140. The vias constitute an example of a configuration for electrically connecting the carbon wires 102 to conductors outside the insulation sheet 104, each of which is here a power source terminal or a signal terminal included in a load 140, for example. The loads 140 will be described later in detail with by way of example.

To the electrical wire 500, the carbon wires 102 included in each of the sheet-shaped system 100 are connected.

The electrical wire 500 in the present embodiment includes a power source line to supply power to illuminating lamps 600 that are used in work in the service tunnel. A power source line being one of the carbon wires 102 included in each sheet-shaped system 100 is connected to the power source line included in the electrical wire 500. Power is thereby supplied to the loads 140 included in each sheet-shaped system 100 via a carbon wire 102 serving as the power source line.

Figure 3:
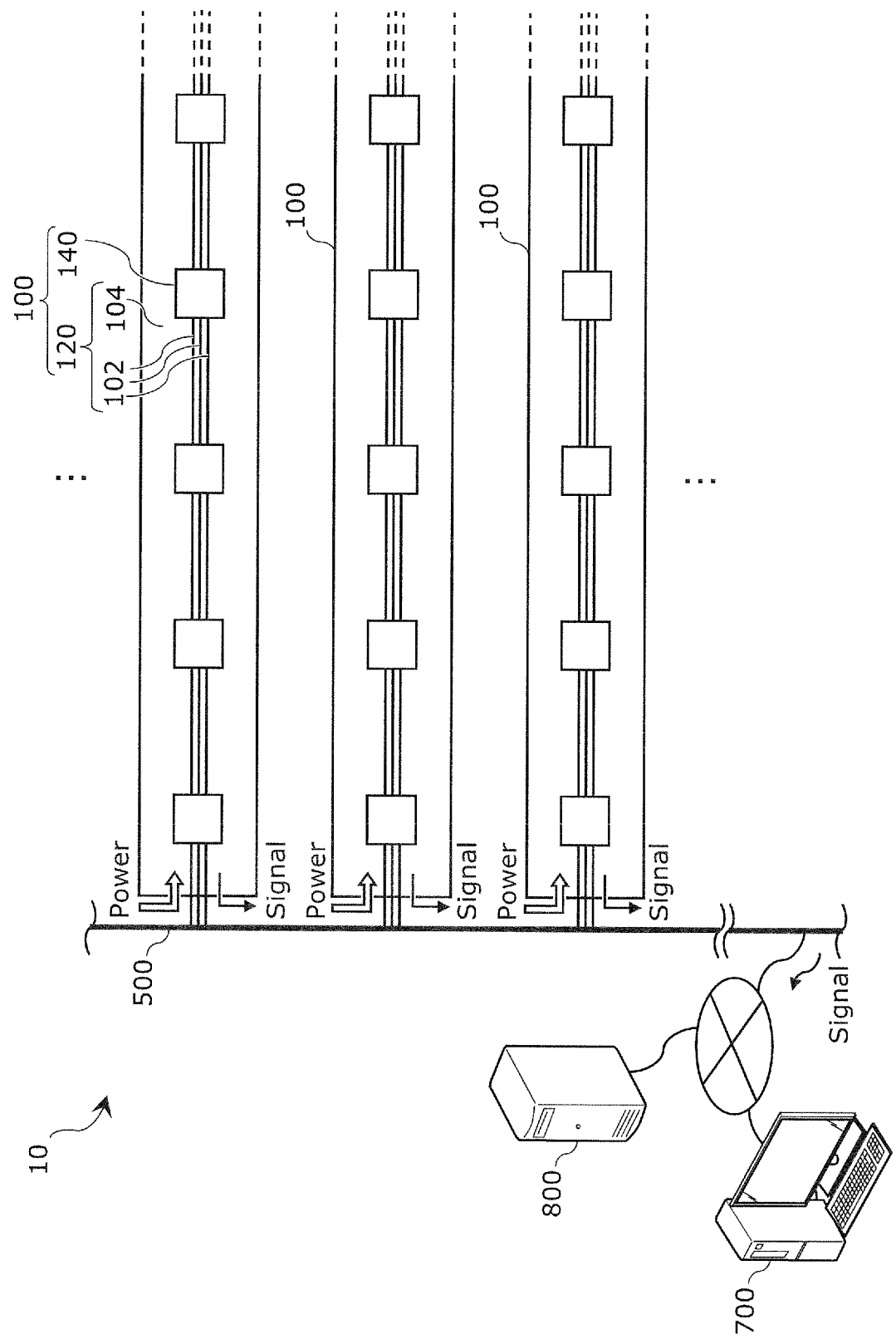
FIG. 3 is schematic diagram illustrating an example of a connection form between constituent components in the above structure operation support system.

The electrical wire 500 in the present embodiment further includes a communication line that is provided for communication with a worker present in the service tunnel. A signal line being one of the carbon wires 102 included in each sheet-shaped system 100 is connected to the communication line included in the electrical wire 500. Signals output from sensors of the loads 140 included in each sheet-shaped system 100 are thereby output via a carbon wire 102 serving as the signal line and carried by a communication line included in the electrical wire 500. The signals are transmitted to a centralized control system with a computer for the service tunnel and are handled by the computer as data to be stored, analyzed, monitored, or the like for grasping a status of the service tunnel. FIG. 3 is a schematic diagram illustrating an example of a form of the connection in the structure operation support system 10 in the present embodiment, which is described thus far.

As illustrated in FIG. 3, each sheet-shaped system 100 includes a plurality of carbon wires 102 that are connected to the electrical wire 500.

The power supplied from the electrical wire 500 are delivered to the loads 140 via carbon wires 102 serving as power source lines.

Carbon wires 102 serving as signal lines are what is called a bus shared by the loads 140 in each sheet-shaped system 100, and the loads 140 are nodes to be connected to the bus. The signals output from the sensors of the loads 140 are output to and carried by the electrical wire 500 via the carbon wires 102. The signals carried by the electrical wire 500 are delivered over a communication network such as the Internet, an intranet, and a private line to a server 800 or a monitoring terminal device 700 included in the centralized control system for the service tunnel. Data represented by the signals are stored in the server 800 or displayed on a monitor of the monitoring terminal device 700.

In a case where a power source line to supply power to illuminating lamps and the like or a communication line is already provided in the structure in which the structure operation support system 10 is installed, as in the example described above, the power source line or the communication line may be used as the power source line or the communication line included in the electrical wire 500. This enables a reduction in an initial cost for the structure operation support system 10.

The configuration described above allows the structure operation support system 10 to include a large number of sensors installed on a surface of a structure and to collect, from the sensors, information indicating the status of the structure. By using data on measurement performed by the sensors at the same time point, it is possible to grasp a spatial status of the structure that is captured at multiple points, which cannot be achieved by a conventional hammering test.

Next, a configuration and operation of the loads 140 each of which includes these sensors and a configuration of the wiring sheets 120 each of which connects a plurality of loads 140 with an electrical wire 500 for a long time will be described.

[1-2. Configuration and Operation of Loads]

Figure 4:
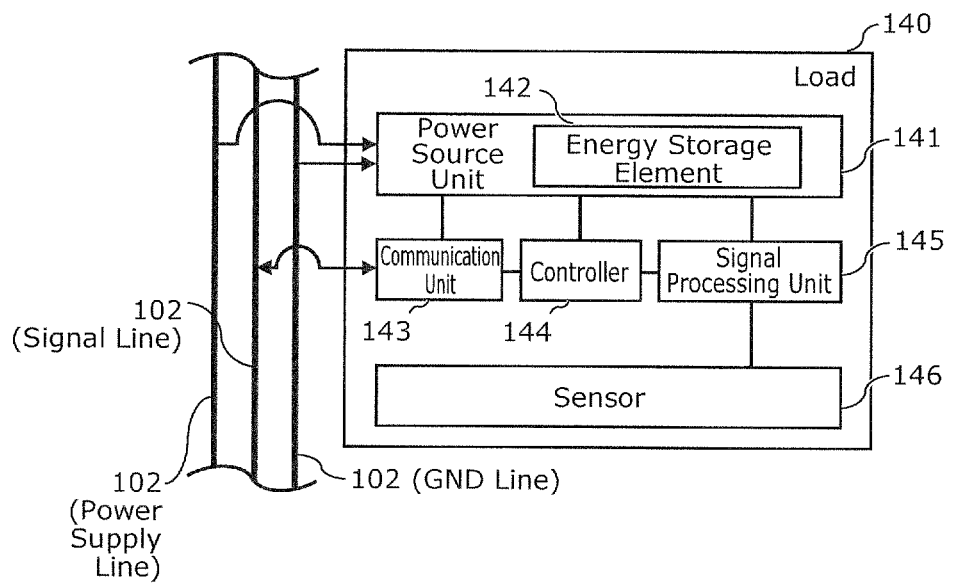
FIG. 4 is a block diagram illustrating a functional configuration example of a load included in the sheet-shaped system according to the embodiment.

FIG. 4 is a block diagram illustrating a functional configuration example of a load 140.

The load 140 includes a power supply unit 141, a communication unit 143, a controller 144, a signal processing unit 145, and a sensor 146.

The power supply unit 141 is a power circuit and generates power to be used for operations of components of the load 140, from input power supplied from the carbon wire 102 serving as a power supply line. The power supply unit 141 in the present embodiment includes a power storage element 142 for storing power to be supplied to the components. The power storage element 142 is provided by using a capacitor or a storage battery. As the power storage element 142, one of long endurance is suitably used. Examples of the power storage element 142 include long-endurance ceramic capacitors and carbon-nanotube capacitors.

The sensor 146 in the present embodiment can be any sensor as long as the sensor is for measuring a physical quantity that is available to grasp various kinds of changes including changes in quality, shape, and the like of a building material to form the structure, such as concrete. For example, the sensor 146 may be a sensor for measuring an amount of iron ions present on the wall surface used to diagnose corrosion of reinforcing iron rods laying inside the wall of the service tunnel, or may be a sensor for measuring a displacement to check whether or how deformation occurs in the wall surface. In addition, various sensors for temperature, humidity, vibration, current, magnetism, electromagnetic wave, electric resistance, specific substances, and the like are used individually or in combination.

Physical quantities measured by the sensor 146 are subjected to processing by the signal processing unit 145 as necessary and output to the communication unit 143 via the carbon wire 102 serving as a signal line to the electrical wire 500 in a form of signals.

The signal processing unit 145 includes, for example, a filter circuit for removing noise, an amplifier circuit for amplifying signals, and an A/D (Analog-to-Digital) conversion circuit for converting analog signals into digital signals.

The communication unit 143 is a communication module that includes an output port for outputting digital signals obtained through processing by the signal processing unit 145 to a signal line.

The measurement performed by the sensor 146 in the present embodiment is not necessarily performed all the time depending on what the measurement is performed on or what a result of the measurement is used, and the measurement may be performed intermittently at given intervals, for example, at predetermine time points of a day. For example, displacements of parts of a structure or corrosion of reinforcing iron rods normally do not progress rapidly in one day. Thus, based on daily measurements, a tendency of the changes can be grasped from stored data on results of the daily measurements. That is, for the measurements, it will suffice that the sensor 146 operates in a very short time, about several seconds or minutes, once to several times a day.

In a case of such an intermittent measurement, for example, it will suffice that power necessary for the operation of each load 140 is stored in the power storage element 142 during an occasion of performing the measurement, and for example, the power may be supplied all the time by a small current.

In a case of such a configuration, the storage of power can be performed by supplying the small current taking a long time, and thus the resistance of the carbon wire 102 may be relatively high. This allows use of inexpensive carbon wires 102, reducing an initial cost of the structure operation support system 10. In addition, use of a small current makes a resistance loss of power, which is in proportion to a square of the current, bringing about a better energy efficiency of the structure operation support system 10 than storing the power in a short time using a large current.

The controller 144 is provided by using, for example, a central processing unit (CPU) and controls operations of the communication unit 143, the signal processing unit 145, and the sensor 146. The CPU includes a timer, and an intermittent operation as with, for example, the measurement described above is performed based on a time kept by the timer. As the CPU, one of low power consumption is suitably used.

The communication unit 143, the controller 144, and the signal processing unit 145 may be provided collectively in a form of one single-chip microcomputer.

To enhance the endurance of the circuit, the load 140 may be encapsulated in glass epoxy or the like except portions of the sensor that need to be exposed for sensing a structure.

As seen from the above, in the burden 140, the electric circuit except that of the power supply unit 141 (operations of the communication unit 143, the signal processing unit 145, and the sensor 146 under control by the controller 144) may perform its operation intermittently receiving power supply from the power storage element 142 according to on what a measurement is performed by the sensor 146 or what a result of the measurement is used. This configuration enables the sheet-shaped system 100 that can carry out necessary functions such as measurements by the sensors to be provided at low cost, and furthermore, enables an initial cost and a running cost of the structure operation support system 10 to be reduced.

[1-3. Configuration of Wiring Sheets]

Figure 5:
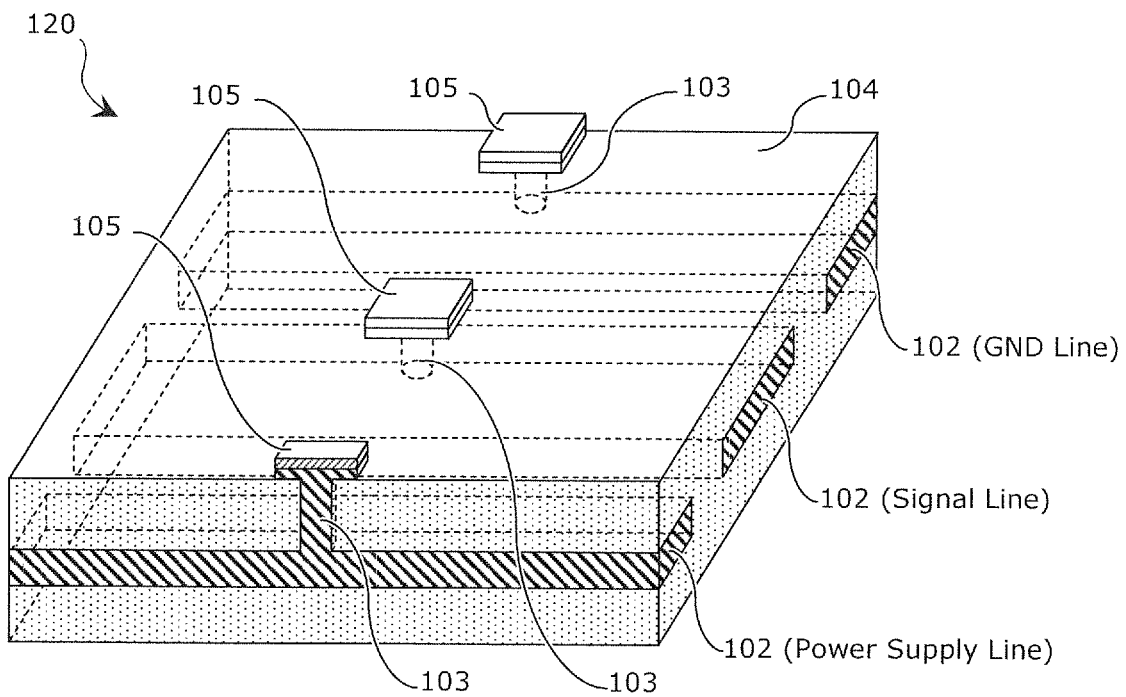
FIG. 5 is a partial cross-sectional view schematically illustrating a configuration example of the wiring sheet according to the embodiment.

FIG. 5 is a partial cross-sectional view schematically illustrating a configuration example of the wiring sheet 120. More specifically, FIG. 5 illustrates a configuration of a spot of the wiring sheet 120 where a load 140 is attached to the wiring sheet 120. The wiring sheet 120 has a plurality of spots having such a configuration.

As illustrated in FIG. 5, in the wiring sheet 120, a plurality of ribbon-shaped carbon wires 102 are enclosed in the insulation sheet 104. This configuration makes the carbon wires 102 less susceptible to an impact from the outside. In addition, in a case where the insulation sheet 104 includes polyvinyl chloride resin as its main material as described above, the carbon wires 102 are additionally less susceptible to moisture, acid, alkali, electricity, and the like.

Since the carbon wires 102 are disposed in the wiring sheet 120 in such a manner as not to come into contact with each other, the carbon wires 102 can stably carry out its function as a power supply line, a signal line, and a GND line. Although the wiring sheet 120 described thus far includes only one carbon wire 102 as a GND line, it is noted that the wiring sheet 120 may include a plurality of carbon wires 102 as GND lines, such as a carbon wire 102 serving as a GND line for a signal ground and a carbon wire 102 serving as a GND line for a frame ground.

In the configuration example illustrated in FIG. 5, the insulation sheet 104 includes a plurality of vias 103 that extends from a surface of the insulation sheet 104 to the carbon wires 102. In this example, the vias 103 include graphene, graphite, single-layer or multilayer carbon nanotube or the like as with the carbon wires 102, and connected to metal terminals 105 on the surface of the insulation sheet 104. A load 140 is connected to the metal terminals 105 on the surface of the insulation sheet 104, so as to be electrically connected to the carbon wires 102 through the vias 103.

Such a wiring sheet 120 can be produced by, for example, a method described below.

First, a solution that is a mixture of carbon material such as graphite and a binder including a macromolecule material is jetted out as in such a manner that a printer paints a given surface with ink, so as be formed to have a sheet shape having a predetermined thickness. When the sheet including carbon material becomes solid, the sheet is cut into a desired shape (e.g., a ribbon shape), and a plurality of carbon wires 102 are thereby obtained.

Next, the plurality of carbon wires 102 obtained in such a manner are arranged so as not to overlap each other, then in this state, sandwiched between sheets including polyvinyl chloride resin and subjected to lamination, and an insulation sheet 104 enclosing the carbon wires 102 is thereby formed.

Next, on the formed insulation sheet 104, a plurality of holes that reaches the carbon wires 102 are opened at positions at which these carbon wires 102 lie inside the insulation sheet 104. Then, the solution described above is applied to the holes so as to fill the holes and applied to surroundings of the holes, to form vias 103. Finally, carbon materials lying upper portions of the filled holes are coupled to metal terminals 105, and the wiring sheet 120 having the configuration illustrated in FIG. 5 is obtained.

Note that the producing method described above is merely an example, and the wiring sheet 120 may be produced by a method that is partially or totally different from the producing method. For example, as the sheet including the carbon material, a commercial sheet or the like including graphite or the like may be used. Alternatively, rather than using the sheet-shaped carbon material, a pattern of carbon wires 102 may be printed on an insulation sheet 104, and the insulation sheet 104 may be folded so that the printed surface is closed therein, or the carbon wires 102 may be sealed by placing another insulation sheet 104 over the insulation sheet 104. The vias 103 may be formed in an insulation sheet 104 before it encloses carbon wires 102. In this case, the carbon wires 102 are disposed so as to extend along the vias 103.

[2. Modifications]

The wiring sheet 120 and the structure operation support system 10 provided with a plurality of wiring sheets 120, according to an embodiment of the present invention, are described above, but the present invention is not limited to the above embodiment. Modifications of the above embodiment will be described, with an example in which the wiring sheets 120, which are used as a part of the sheet-shaped system 100, are used individually, and an example in which the sheet-shaped systems 100, which are connected to the electrical wire 500 to form the structure operation support system 10, are used individually.

[2-1. Modification 1]

The configuration of the wiring sheet 120 is not limited to one illustrated in FIG. 1 to FIG. 3 that includes the three carbon wires 102 serving as a power supply line, a signal line, and a GND line, and the elongated insulation sheet 104 encloses these lines separately. For example, the wiring sheet 120 may have a shape unfoldable vertically and horizontally, like wallpaper. In addition, the insulation sheet 104 may include various kinds of carbon wires 102 that include a plurality of power source lines and a plurality of signal lines, and the like, and the various kinds of carbon wires 102 may cross each other on multiple levels as long as the various kinds of carbon wires 102 are insulated from each other.

[2-2. Modification 2]

Figure 6A:
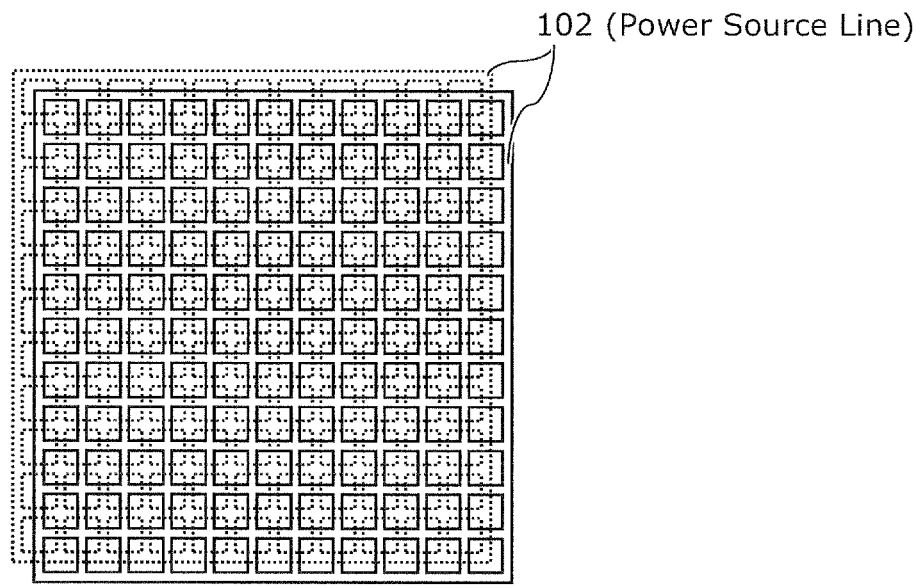
FIG. 6A is a schematic diagram illustrating an example of shapes of carbon wires in Modification 2 of the embodiment.
Figure 6B:
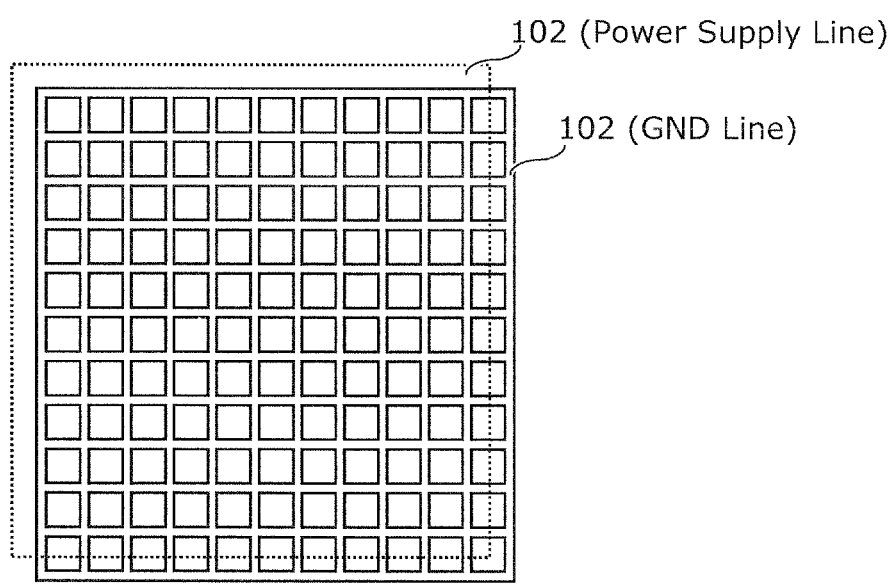
FIG. 6B is a schematic diagram illustrating another example of the shapes of carbon wires in Modification 2 of the embodiment.
Figure 6C:
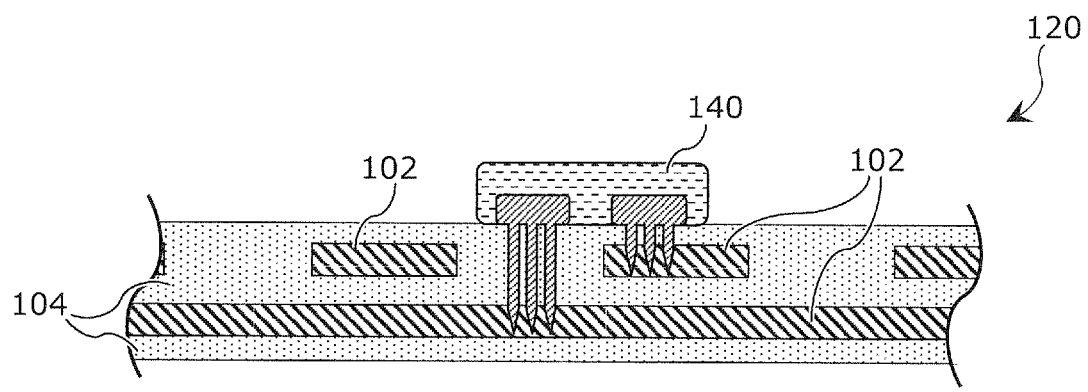
FIG. 6C is a schematic partial cross-sectional view of a wiring sheet including the carbon wires according to Modification 2 of the embodiment.

The carbon wires 102 described thus far each provide a linear, one-dimensional-shape electrical pathway but each may provide a two-dimensional-shape electrical pathway. FIG. 6A and FIG. 6B are both schematic diagrams each illustrating an example of shapes of carbon wires 102 that are power source lines in Modification 2. FIG. 6C is a schematic partial cross-sectional view of a wiring sheet 120 that include such carbon wires 102. Solid lines and broken lines in FIG. 6A and FIG. 6B are used to separately indicate two carbon wires 102 that, except part of them, overlap with each other being arranged in a front-to-back direction or a vertical direction.

A carbon wire 102 serving as a power source line may form a grid, as illustrated in FIG. 6A for example. Of the two carbon wires 102 in FIG. 6B, one is a power supply line and the other one is a GND line. In the wiring sheet 120, these carbon wires 102 are in a positional relationship in which one carbon wire 102 is seen through holes of a grid of the other carbon wire 102 and, as illustrated in FIG. 6C, the carbon wires 102 are separated from each other with the insulation sheet 104 interposed therebetween. Being in such a positional relationship, both of the carbon wires 102 can be accessed across a wide area with a surface of the wiring sheet 120 that is exposed when the wiring sheet 120 is attached to a wall surface.

For example, as illustrated in FIG. 6C, a load 140 may include conductive, needle-shaped terminals, and the terminals may be made to pierce the insulation sheet 104 at proper positions on a surface of the insulation sheet 104, so as to come into contact with both of the carbon wires 102. By disposing three or more needle-shaped terminals to be connected to the carbon wires 102 such that they are close to each other, it is possible to cause the terminals to apply pressure to each other, yielding a good contact with the carbon wires 102.

A two-dimensional-shape electrical pathway including such carbon wires 102 has a resistance lower than that of a one-dimensional-shape pathway including one linear carbon wire 102. As such, when the electrical pathway is used as a power source line, power can be carried more effectively. On a wiring sheet 120 that encloses such carbon wires 102 and extends two-dimensionally, a spot to take power can be selected with a high degree of freedom. Such a configuration of a wiring sheet 120 is applicable to, for example, wallpaper or the like. When a wall surface of a room or the like is covered with this wallpaper, and the carbon wire 102 is connected to a power source, it is possible to take power at different spots on the wall surface. In addition, such wallpaper allows for providing spots to attach a load including an electric circuit across a wide area without performing work such as drilling a wall, making it easy to introduce an IoT technology to connect many things to a network at many spots. In addition, such a configuration of a wiring sheet 120 is applicable to a thing that is smaller than wallpaper and used being unfolded into a sheet shape, for example, a tablecloth.

In addition, as illustrated in FIG. 6B, by forming one of the two carbon wires 102 used as a power supply line into a sheet shape, a wiring sheet 120 that has an even lower resistance and a higher degrees of freedom in selecting a position to attach a load is obtained.

The present modification is described thus far using an example in which the carbon wires 102 are used only as power source lines. The load 140 attached to such a wiring sheet 120 can perform communication, for example, wirelessly. The carbon wires 102 in the present modification can be used as signal lines. In a case of circumstances that makes it difficult for a signal line and a power source line to coexist, a configuration in which loads 140 each include an energy harvesting device such as a solar cell.

[2-3. Modification 3]

The wiring sheet 120 may be used not only for installing sensors or the like as described in Embodiment but also in various applications aiming power supply or signal transmission.

For example, in a structure such as a house and a building or in a facility such as an underground shopping arcade, the wiring sheet 120 may be attached to part of or the whole of a wall in a room to install a line for power supply or signal transmission. In this case, for example, a carbon wire 102 serving as a power source line may be connected to a commercial power, and a carbon wire 102 serving as a signal line may be connected to a telephone line or a broadcast receiving antenna. In addition, to the vias 103, terminals for connection to a device that takes and uses power or signals from the carbon wires 102 may be attached. A location with such a wiring sheet 120 installed has a high degree of freedom in selecting spot to take power, or signals from a communication line and a broadcast receiving antenna. That is, the place has a high degree of freedom in disposing an electrical apparatus, reducing a possibility that an extension cable or the like is needed.

When the wiring sheet 120 is used in such a manner, for example, resins such as polyvinyl chloride resin and polyolefin, cloth, paper, glass fiber or the like may be used as a material for the insulation sheet 104 being a flexible electrical insulator. This enables the wiring sheet 120 to meet a demand for appearance in an installation location.

[2-4. Modification 4]

The vias 103 need not be provided in the insulation sheet 104 in advance, and for example, holes may be opened on the insulation sheet 104 at only spots to take power or signals, on an as-needed basis. For example, a hole may be opened with a conductor with a needle-shaped end, with which an electrical apparatus being a load 140 that receives power from or exchange signals with carbon wires 102 is electrically connected with the carbon wires 102. Such a via 103 has an effect of enhancing a degree of freedom in disposition and an effect of simplifying wiring from a power source or the like particularly for an electrical apparatus that is mounted on a wall when used. Alternatively, only a plurality of holes that reach the carbon wires 102 may be provided, and detachable plugs may close the holes. In this case, after installation, a plug at a spot to take power and signals may be removed, and the exposed carbon wires 102 may be connected to an electrical apparatus.

Such a wiring sheet 120 provides a wiring for power supply or signal transmission that can be used for a long time while meeting various demands for appearance of installation locations. In addition, such a wiring sheet 120 enables enhancement of a degree of freedom in disposing an electricity product and simplification of wiring between an electrical apparatus and a power source or the like.

Figure 7:
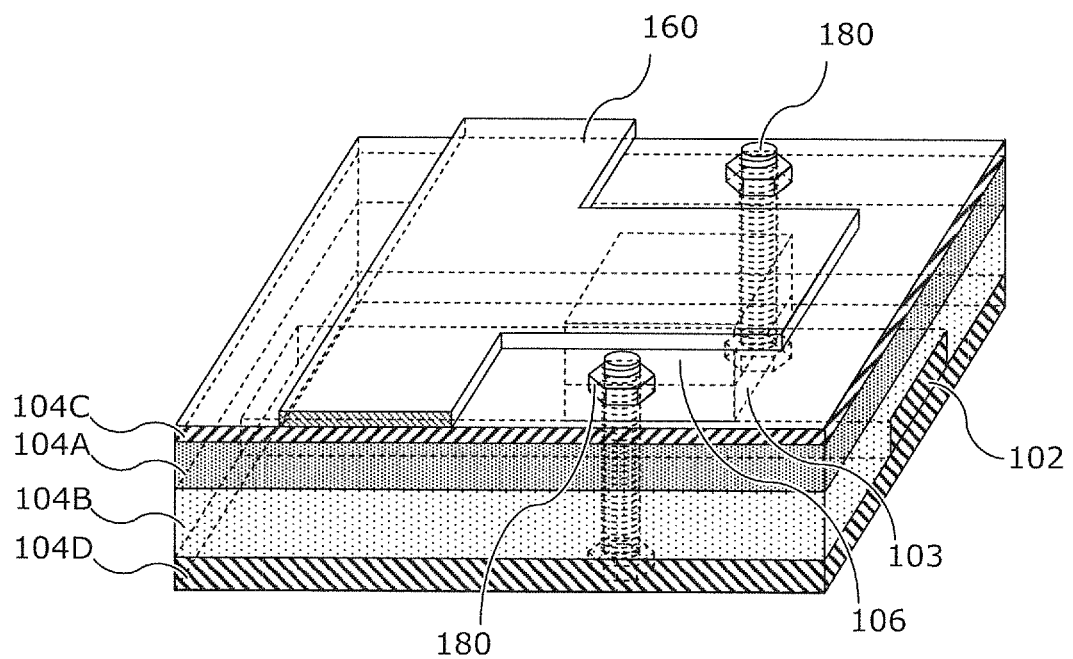
FIG. 7 is a schematic partial cross-sectional view illustrating a configuration example of a wiring sheet that electrically connects a carbon wire in an insulation sheet and an outside conductor using a contact including anisotropic conductive rubber, in Modification 4 of the embodiment.

Some material of the insulation sheet 104, some location to install the wiring sheet 120, or the like may fail to provide a required reliability of an electrical connection between carbon wires 102 in an insulation sheet 104 and an outside load 140 when the connection is made by hard things such as the vias 103. To improve the reliability, a conductor outside the insulation sheet 104 and the carbon wires may be electrically connected with contacts including anisotropic conductive rubber. FIG. 7 is a schematic partial cross-sectional view illustrating a configuration example of a wiring sheet 120 that electrically connects a carbon wire 102 in an insulation sheet 104 and an outside conductor with a contact including anisotropic conductive rubber. The entire surface of the insulation sheet 104 need not have such a configuration, and the insulation sheet 104 may be configured as such only at a spot to install a load 140.

In the present modification, the insulation sheet 104 includes a contact 106 to connect the carbon wire 102 and an outside wiring. The contact 106 is in a plate shape or a cylindrical shape, and includes one surface (or one end surface) that is exposed to a surface of the insulation sheet 104 and the other surface (or the other end surface) that is electrically connected to the carbon wire 102.

The contact 106 includes anisotropic conductive rubber as described above. Anisotropic conductive rubber contains conductive pins or particles at a given density and becomes conductive only when receiving a pressure in a predetermined direction. The contact 106 in the present modification becomes conductive only when receiving a pressure in a thickness direction of the insulation sheet 104. In the example illustrated in FIG. 7, there is a carbon-made via 103 between the carbon wire 102 and the contact 106. The contact 106 and the via 103 may be used in combination in this manner, or only one of them may be used.

In addition, the insulation sheet 104 includes an insulation sheet first layer 104A and an insulation sheet second layer 104B. In the example illustrated in FIG. 7, the insulation sheet first layer 104A has a thickness that is substantially the same as a thickness of the carbon wire 102 and the carbon via. The insulation sheet first layer 104A may have a larger thickness that is enough to cover a bottom surface of the carbon wire 102 in FIG. 7.

In contrast, the insulation sheet second layer 104B placed on the insulation sheet first layer 104A preferably has a thickness that is smaller than that of the contact 106. This is to make a part of contact 106 to protrude from the insulation sheet second layer 104B so as to make it easy to apply the pressure in the thickness direction of the insulation sheet 104, which is necessary for the contact 106 to become conductive, to the contact 106.

The insulation sheet first layer 104A and the insulation sheet second layer 104B both include, for example, organic macromolecule materials being insulators. The insulation sheet second layer 104B is however somewhat harder than the insulation sheet first layer 104A. This is because the insulation sheet second layer 104B braces the contact 106 receiving the pressure so that the contact 106 does not move.

For example, assume a load 140 that includes a terminal on its bottom surface and includes a hole to screw the load 140 on a wall surface or the like. In a wiring sheet 120 attached to a wall surface, the load 140 is screwed on the wall surface in such a manner as to press the wall surface via the wiring sheet 120, with this terminal brought into contact with the contact 106 by a part having the above configuration. The contact 106 is thereby receives the pressure to become conductive, by which the terminal of the load 140 is electrically connected to the carbon wire 102 in the wiring sheet 120 via the contact 106.

With an elasticity of the anisotropic conductive rubber, the contact 106 easily comes in contact with this terminal by a larger area, which enables the terminal and the wiring sheet 120 to be electrically connected more reliably. In addition, the use of the contact 106 including the anisotropic conductive rubber also provides an effect of insulating the carbon wire 102 inside the insulation sheet as with spots covered by the insulation sheet when no load is connected.

Note that the example illustrated in FIG. 7 has a configuration still different from the above, where a conductor outside the insulation sheet 104 is electrically connected to the carbon wire 102 in the insulation sheet 104 by applying a pressure to make the contact 106 conductive.

The insulation sheet 104 further includes an circuit board 104C and a support member 104D that form layers sandwiching the insulation sheet first layer 104A and the insulation sheet second layer 104B. The circuit board 104C and the support member 104D are both insulators harder than the insulation sheet first layer 104A.

The circuit board 104C has a through hole, through which the part of the contact 106 protruding from the insulation sheet second layer 1048 extends to be exposed. The exposed part of the contact 106 comes into contact with a wiring 160 outside the insulation sheet 104 that extends on a circuit board 104C. Note that the wiring 160 is actually fixed and integrated into the circuit board 104C but assumed to lie outside the insulation sheet 140 for convenience of description. Such a wiring 160 may be provided to, for example, connect a plurality of terminals of a load 140 and a plurality of carbon wires 102 while offsetting a difference between a distance across the terminals of the load 140 and a distance across the carbon wires 102. The wiring 160 may be replaceable according to different circuit boards 104C so as to cover the distance across the terminals of the load 140 to be attached to the wiring sheet 120.

The support member 104D supports the carbon wire 102 directly or via the insulation sheet first layer 104A from an side of the carbon wire 102 in the insulation sheet 104 opposite to the circuit board 104C.

To attach the outside conductor, the wiring 160 in this example, pressurization mechanisms 180 that extends through from the circuit board 104C to the support member 104D is used to clamp the insulation sheet 104 with a force in the thickness direction of the insulation sheet 104, as illustrated in FIG. 7.

This applies a pressure to make the contact 106 conductive from the wiring 160, by which the wiring 160 is electrically connected to the carbon wire 102 in the insulation sheet 104 via the contact 106. The pressurization mechanisms 180 illustrated in FIG. 7 are each formed of a bolt and a nut but may be anything that can be used to clamp the insulation sheet 104 in the thickness direction and can be replaced with, for example, grommets, swages, rivets, staplers, or the like.

Such a configuration also provides the same effects as those of the present modification described above.

[2-5. Modification 5]

The wiring sheet 120 in the embodiment and some of its modifications includes a plurality of carbon wires 102 each of which serves as a power supply line, a signal line, or a GND line, but the wiring sheet 120 need not include some of these carbon wires 102 depending on a usage environment and application of the wiring sheet 120. That is, the wiring sheet 120 need not include a power supply line and may be used only to provide a signal line in its installation location. Contrariwise, the wiring sheet 120 need not include a signal line and may be used only to provide a power supply line in its installation location.

In addition, the applications of the carbon wires 102 included in one wiring sheet 120 and the number of carbon wires 102 for each application are not limited to those of the embodiment and the modifications of the embodiment. For example, one wiring sheet 120 may include a plurality of signal lines, where applications of the signal lines are separated, including a signal line for carrying clock signals and a signal line for carrying data signals. The clock signals are transmitted from, for example, a gateway or a master device described later.

In addition, the above carbon wires 102 are all connected to the electrical wire 500, but the sheet-shaped system 100 may further include a carbon wire 102 that does substantially not transmit current but is used to establish a ground, so to speak as a Kelvin ground connection. In the present specification and the like, this line for the Kelvin ground connection is referred also to as a second GND line to draw a distinction from the above first GND line through which current flows.

For example, in a case where a surface potential of a structure that is an installation location of the sheet-shaped system 100 is measured using the sensor 146 included in the load 140, establishing the grounding potential using the first GND line raises a problem in that a voltage drop attributable to a resistance of the carbon wire 102, which is relatively larger than common conductive lines including copper or the like, and the surface potential cannot be obtained accurately due to an influence of the voltage drop.

Figure 8:
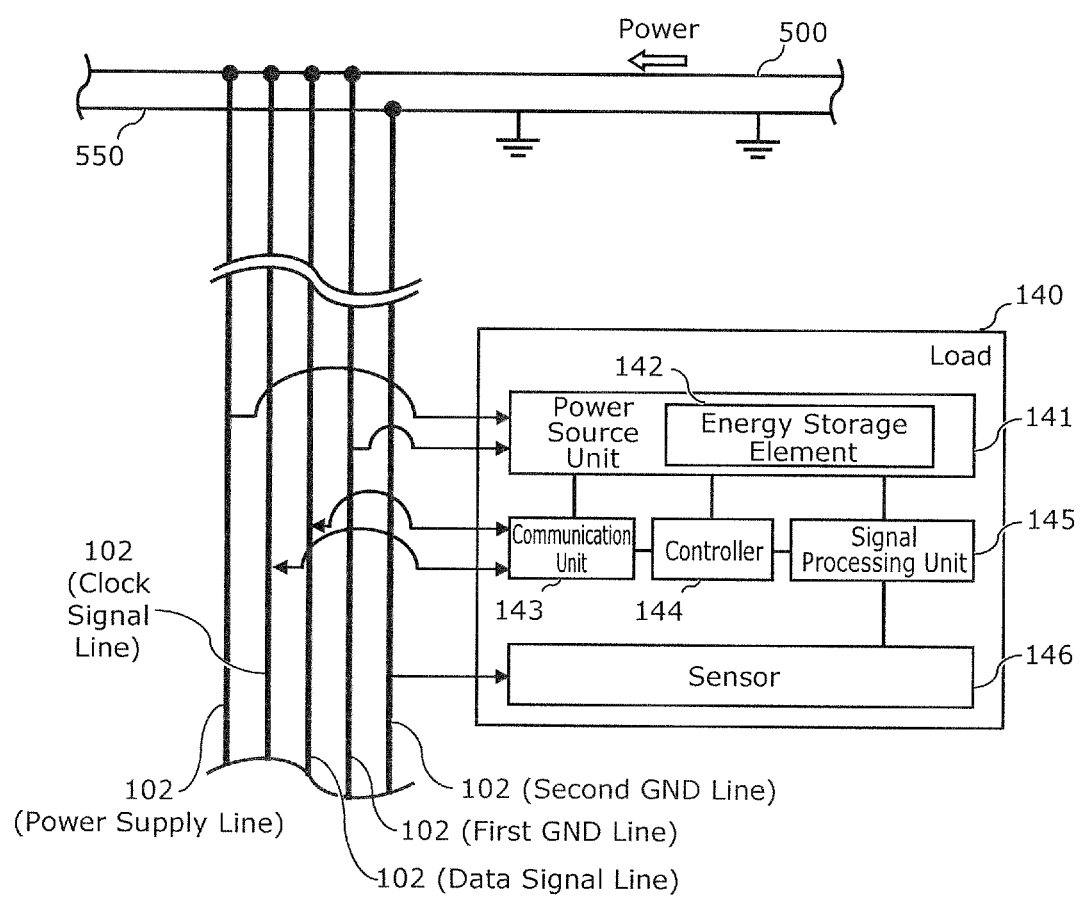
FIG. 8 is a block diagram illustrating a connection example of a second GND line in Modification 5 of the embodiment.

This problem can be solved by using a configuration in which the load 140 uses the grounding potential established by the Kelvin ground connection as a reference potential for the measurement using the sensor 146. FIG. 8 is a block diagram illustrating an example of how the second GND line is connected in a sheet-shaped system 100 having such a configuration.

In the example illustrated in FIG. 8, the sheet-shaped system 100 includes five carbon wires 102. Of the carbon wires 102, one serves as the second GND line. The second GND line is connected not to the electrical wire 500 to supply power but to a ground line 550 that is not connected to a power source at all and is grounded via the ground line 550. For example, the ground line 550 may be connected at some places to reinforcing iron rods included in a wall of the structure in which the sheet-shaped system 100 is installed. At the same time, the second GND line is connected to the sensor 146. With this configuration, the load 140 can measure a surface potential of a measurement object by determining a difference between a potential sensed by the sensor 146 and a potential of the second GND line

[2-6. Modification 6]

The load 140 of the sheet-shaped system 100 in the above embodiment include a sensor and may include, in addition to or in place to the sensor, another electrical load according to an application of the sheet-shaped system 100.

For example, the load 140 may include a light source such as a light emitting diode, and the light source may be turned on in response to a result of sensing by the sensor or to provide a light necessary for the sensing by the sensor. Alternatively, the sheet-shaped system 100 including the load 140 with the light source may be used as a lighting fixture. In addition, the electrical load included in the load 140 is not limited as long as the electric load operates on power, and may be a driving device such as a motor and an actuator, a sound emitting device such as a buzzer, a heat emitting device, or the like.

The structure operation support system 10 including such a sheet-shaped system 100 can be used for maintenance of a structure, as well as a system for illuminating or decorating the structure. Alternatively, such a structure operation support system 10 can be used as a system to build an environment to support various kinds of operations of the structure, for example, an environment for a predetermined purpose, such as experiment, cultivation of plants, and keeping animals. Also in this case, the structure operation support system 10 reduces an initial cost or a running cost and, with its high reliability and high endurance, contributes to increasing an operating rate of the structure as a facility for the predetermined purpose.

In a case where power necessary for operation of the electric circuit of the load 140 is supplied from the carbon wire 102 at any time, the load 140 need not include the power storage element 142 in the embodiment and the modifications of the embodiment.

[2-7. Modification 7]

In the embodiment, the wiring sheet 120 in the sheet-shaped system 100 measures about 10 m in its long-side direction, as an example. In addition, the resistance of the carbon wire 102 is about 1 ohm per centimeter, as an example.

In a case where the sheet-shaped system 100 having such scales is operated in a form illustrated in FIG. 2, a distance from a connecting portion between the sheet-shaped system 100 and the electrical wire 500 to an end of the carbon wire 102 is about 5 m, and a resistance therebetween is 500 ohms. Here, assuming that, for example, a peak current of the load 140 is 20 mA, a voltage drop of 10 V occurs between the connecting portion and the end of the carbon wire 102. An influence of a voltage drop occurring in such a manner due to a large resistance of the carbon wire 102 serving as a power supply line raises a problem in that some loads 140, particularly those close to the end of the carbon wire 102 cannot be charged by a necessary amount between their intermittent operations.

Figure 9:
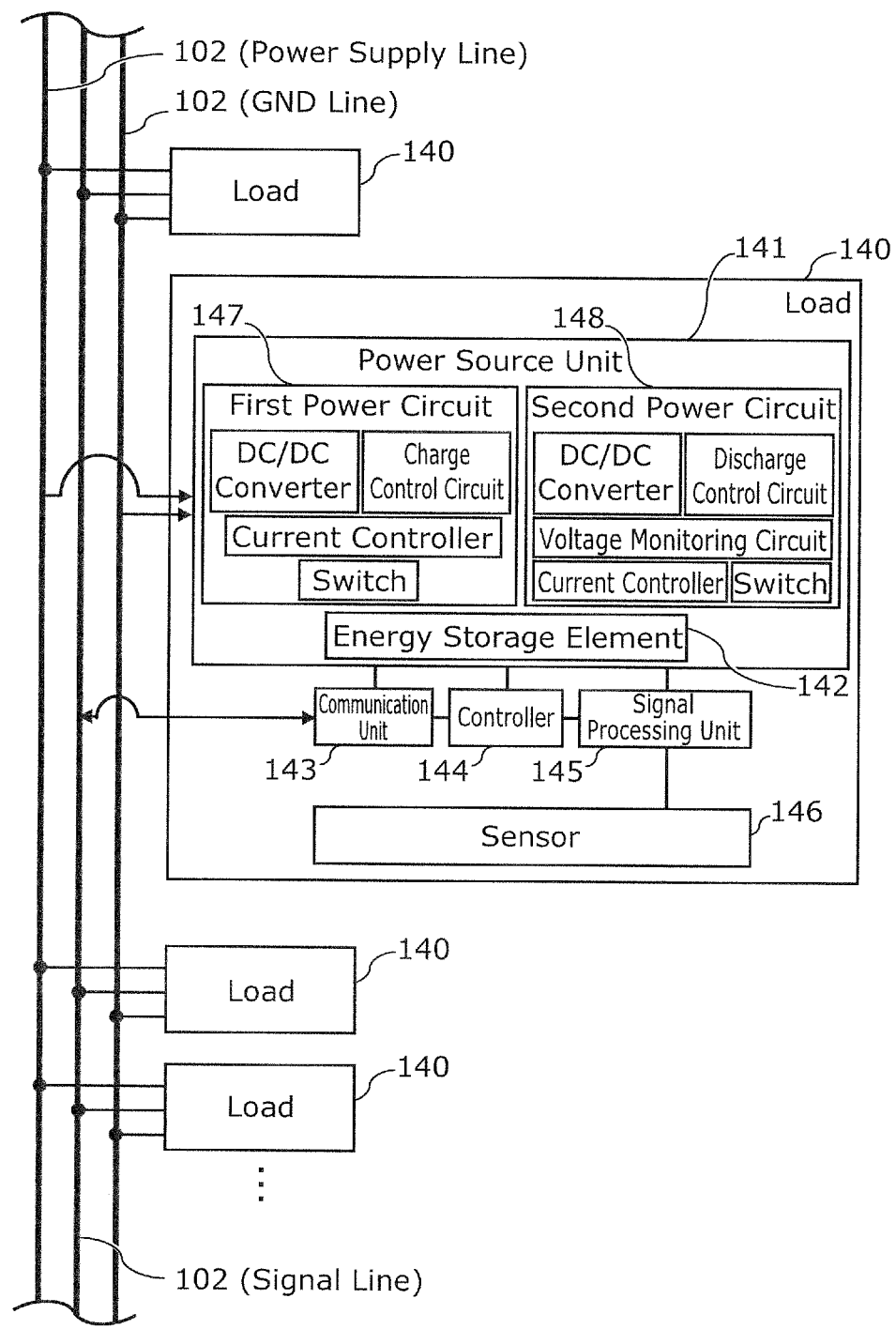
FIG. 9 is a block diagram illustrating a functional configuration of a load included in a sheet-shaped system according to Modification 7 of the embodiment.

To solve such a problem, the sheet-shaped system 100 may be configured to allow neighboring loads 140 that share the power supply line to interchange their power when possible. FIG. 9 is a block diagram illustrating a functional configuration of loads included in such a sheet-shaped system 100. Description will be made below focusing differences from the functional block diagram of the embodiment illustrated in FIG. 4.

The loads 140 in the present modification differ from the loads 140 in the embodiment in the configuration of the power supply unit 141. The loads 140 in the present modification each include, in the power supply unit 141, two power circuits that are functionally different from each other, a first power circuit 147 and a second power circuit 148.

The first power circuit 147 is a power circuit for obtaining power from the carbon wire 102. The first power circuit 147 includes a DC-DC converter, a charge control circuit, a current controller, and a switch.

The DC-DC converter adjusts a voltage difference between an inside and an outside of the load 140. The charge control circuit controls a charge of the energy storage element 142 and prevents overcharge. The current controller and the switch controls whether to flow current from the carbon wire 102 to the power storage element 142, a load circuit such as the sensor, or to flow current from the power storage element 142 to the load circuit.

The second power circuit 148 is a power circuit for returning power to the carbon wire 102. The second power circuit includes a DC-DC converter, a discharge control circuit, a voltage monitoring circuit, a current controller, and a switch.

The DC-DC converter adjusts a voltage difference between an inside and an outside of the load 140. The discharge control circuit controls discharge from the power storage element 142 and prevents overdischarge. The voltage monitoring circuit monitors a voltage of the carbon wire 102. The current controller and the switch controls whether to flow current from the power storage element 142 to the carbon wire 102, based on whether a predetermined condition is satisfied.

For example, assume a case where the loads 140 sharing a power supply line are disposed 1 m apart in the sheet-shaped system 100 where the above distance from the connecting portion with the electrical wire 500 to the end of the carbon wire 102 is about 5 m. In this case, when a current of 10 mA is given from a load 140 to an adjacent load 140 1 m apart, the voltage drop is suppressed to 10 mA×100 ohms=1 V. The load 140 given the current can operate its sensor or charge its power storage element 142.

This can enhance stability of the operation of the sheet-shaped system 100 as a whole. In addition, even in the sheet-shaped system 100 that is longer in its entire length and includes the carbon wires 102 having high resistances, or even in the sheet-shaped system 100 that is the same size but includes carbon wires 102 being inexpensive but high in resistance, the problem of supplying power to the loads 140 is solved, enabling practical operation.

[2-8. Modification 8]

In Modification 7, the problem of a voltage drop due to using the carbon wires 102 having high resistances is introduced, and the configuration to solve the problem is described. The present modification is also for solving the problem of a possible voltage drop.

Description will be made using the sheet-shaped system 100 assumed as the example in Modification 7 again. Assume that the sheet-shaped system 100 includes ten loads 140, as illustrated in FIG. 2. When all of the loads 140 are changed simultaneously with a current of 1 mA, a voltage drop of 10×1 mA×500 ohms=5 V occurs. The voltage drop can cause a problem of poor charging or inability to perform charging as in Modification 7.

Figure 10A:
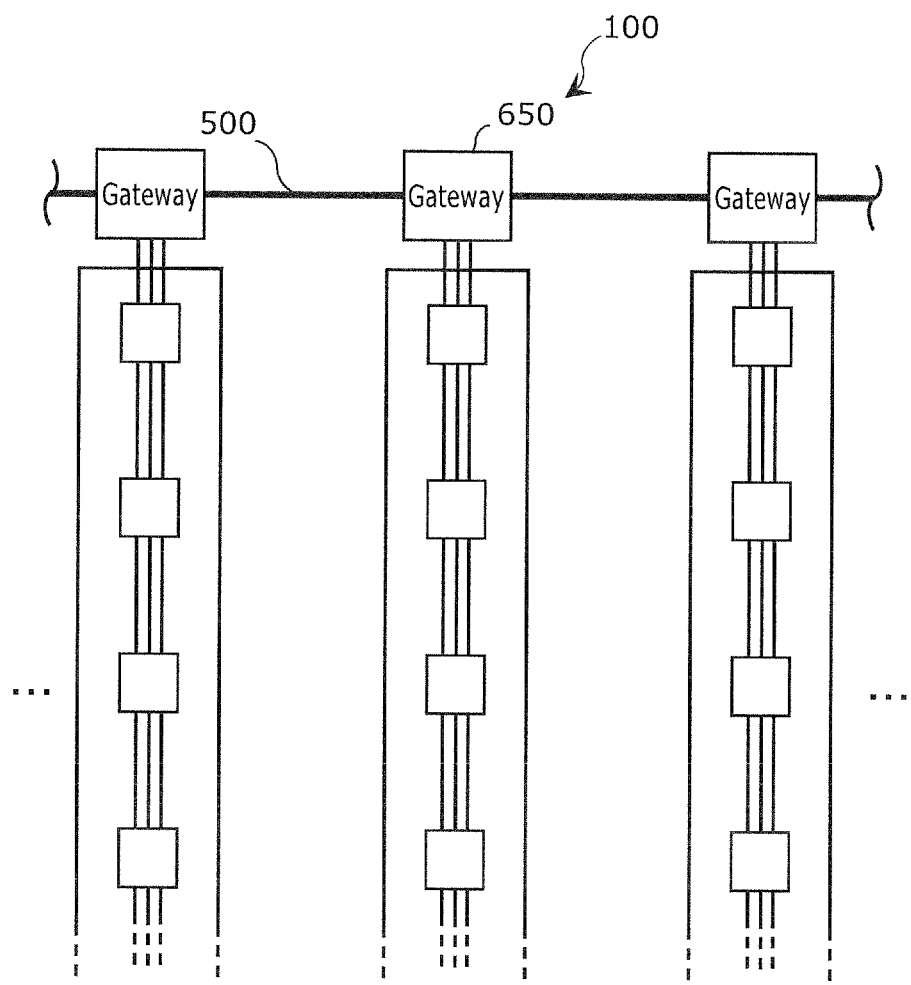
FIG. 10A is a schematic diagram used for describing a configuration of a sheet-shaped system according to Modification 8 of the embodiment.
Figure 10B:
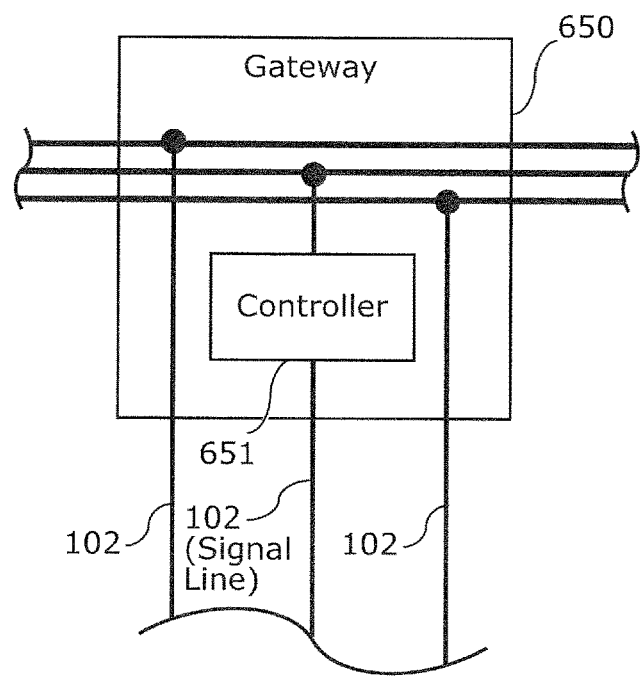
FIG. 10B is a block diagram illustrating a functional configuration example of a gateway included in a sheet-shaped system according to Modification 8 of the embodiment.

To solve such a problem, the sheet-shaped system 100 may be configured to limit the number of loads 140 that consumes power for charging or the like simultaneously. FIG. 10A is a schematic diagram used for describing a configuration of such a sheet-shaped system 100. FIG. 10B is a block diagram illustrating a functional configuration of a gateway 650 included in such a sheet-shaped system 100.

The sheet-shaped system 100 according to the present modification includes gateways 650.

The gateways 650 electrically connects the electrical wire 500 through which electricity from a power source outside the sheet-shaped system 100 flows to a carbon wire 102 serving as a power supply line. The gateways 650 each include a controller 651 as illustrated in FIG. 10B. The control section 651 is provided by, for example, use of a microcontroller including a CPU, a memory, a timer, and an input/output unit and is connected to a carbon wire 102 serving as a signal line with the input/output unit interposed therebetween.

In this configuration, the gateways 650 transmit instructions on supplying power to the loads 140. More specifically, instructions on whether to receive the supply of power from the outside power source via the power supply line are given to each of the loads 140 of the sheet-shaped system 100. Receiving the instructions, the loads 140 each start or stop receiving the power supply according to the instructions.

The gateway 650 may allow the loads 140 included in one sheet-shaped system 100 to receive the supply of power in turn, for example, every time a certain time period elapses. Alternatively, in consideration of the voltage drop described in Modification 7, the gateway 650 may allow loads 140 close to the end of the carbon wire 102 to receive the supply of power for a longer time. In addition, the gateway 650 may receive notifications about states of charge of the power storage elements 142 of the loads 140 and preferentially allow loads 140 having low states of charge to receive the supply of power.

Such instructions are issued so as to limit the number of loads 140 that receive the supply of power simultaneously. For example, the gateway 650 limits the number of loads 140 receiving the supply of power so that the voltage drop is suppressed to within a predetermined range of a power supply voltage so that an influence of the voltage drop on charging the loads 140 does not become excessively significant. Charging is thereby normally performed on the loads 140 of the sheet-shaped system 100, enabling a proper operation. In addition, it is possible to enhance the stability of the operation of the sheet-shaped system 100 as a whole.

Communication between the gateway 650 and the loads 140 is not limited to wired communication via the signal line and may be performed by wireless communication.

[2-9. Modification 9]

There is no description thus far about functional differences between the plurality of loads 140 included in each sheet-shaped system 100 but all of the loads 140 do not have to be functionally equivalent. For example, one of the plurality of loads 140 may play a role of a master device, collect results of sensing by the other loads 140 as slave devices, and output the results to the electrical wire 500.

[2-10. Modification 10]

In the embodiment, the distance between the wiring sheets 120 in the sheet-shaped system 100 is about 10 m, as an example. The distance between the wiring sheets 120 may be however shorter according to location or purpose of using the sheet-shaped system 100.

However, when the carbon wires 102 used as signal lines become long, the carbon wires 102 act as antennas under an influence of carried signals and prone to emit radio waves. The radio waves may be a cause of radio interference such as causing signal lines included in another nearby sheet-shaped system 100 to produce noise and causing a misoperation or the like of an electronic device. In particular, harmonic components, such as ones that are contained in a square-wave and have alternating rates of repetition higher than an alternating rate of a signal, tends to raise this problem.

To solve this problem, in a case where the wiring sheet 120 includes three or more carbon wires 102 including a power supply line, a signal line, and a first GND line, the power supply line, the signal line, and the first GND line may be disposed in the insulation sheet 104 such that they lie in parallel to each other and the signal line is positioned between the power supply line and the first GND line.

This reduces harmonic components contained in a signal in the signal line that cause the radio interference, through a capacity coupling between the signal line and the power supply line and a capacity coupling between the signal line and the first GND line.

Figure 11:
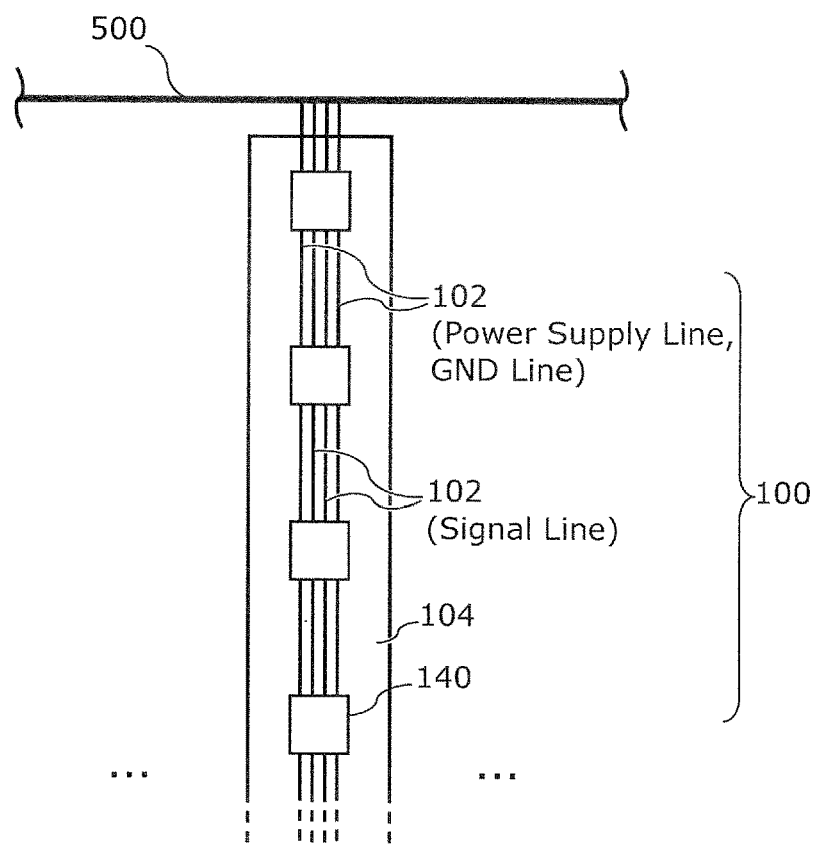
FIG. 11 is a schematic diagram used for describing an example of disposing carbon wires in a wiring sheet according to Modification 10 of the embodiment.

FIG. 11 is a schematic diagram used for describing an example of how such carbon wires 102 are disposed. In this example, a wiring sheet 120 includes four carbon wires 102, one of which is power supply line, one of which is a GND line, and the other two of which are signal lines for carrying data signals and clock signals. The two carbon wires 102 serving as the signal lines extend in parallel to each other in the wiring sheet 120 and are sandwiched between the other two carbon wires 102. The other wiring sheets 120 in FIG. 11 also have the same configuration, and neighboring sheet-shaped systems 100 mutually prevent radio interference from occurring.

Even in a case where none of the carbon wires 102 included in the wiring sheet 120 is not used as a power supply line, or a case where carbon wires 102 cannot be disposed in parallel to each other, the harmonic components can be suppressed by a method to collapse a shape of a driving wave.

[2-11. Modification 11]

In the service tunnel being a usage environment described above, there are many noises caused by a large number of cables and the like through which electricity passes. Signals representing a result of sensing by the sensor 146 included in the sheet-shaped system 100 or the structure operation support system 10 installed in such an environment are preferably transmitted in a wired manner through a carbon wire 102 serving as a signal line.

However, in a case where the sheet-shaped system 100 or the structure operation support system 10 installed in an environment with less noises or an environment where a distance from a target of communication is limited to about several meters, the communication unit 143 may include a function of wireless communications and transmit in a wireless manner. In this case, when the power storage element 142 is a power source for the operation of the electric circuit of the load 140, the communication unit 143 is preferably implemented with a communication module of Bluetooth® Low Energy, or the like that performs communication with lower power consumption. For example, in each sheet-shaped system 100, the load 140 being a master device described in 2-9 may receive and collect the results of sensing by the other loads 140 being slave devices in a wireless manner, and output the collected results to the electrical wire 500 to transmit the results to a remote centralized control system.

In addition, the description of the above embodiment only shows the case where the loads 140 transmit signals but the loads 140 may receive signals. For example, the loads 140 may receive signals for an operation test, a temporary operation, or the like from the centralized control system for the service tunnel or the like via the electrical wire 500 and the carbon wires 102 being signal lines. Alternatively, for example, the loads 140 may perform bidirectional communication with an information terminal device held by a worker in the service tunnel, and perform measurement corresponding to an operation of the worker and transmits a result of the measurement.

[2-12. Other Modifications]

Major modifications of the above embodiment are described in the above 2-1 to 2-11, and there are still other possible various modifications that are not described specifically in the above description.

For example, the sheet-shaped systems 100 described above all include a plurality of loads but the number of loads included in each sheet-shaped system 100 may be one.

In addition, as the material of the insulation sheet 104, natural resin rubber, which is a typical insulator, may be used.

In addition, the material of the vias 103 is not limited to a carbon material such as graphite and may be any conductive body that can endure an environment of the installation location for a long term.

In addition, Examples of the structure being the installation location of the structure operation support system 10 include buildings such as the above service tunnel, houses, buildings, and commercial facilities, as well as poles, steel towers, dams, bridges, roads, embankments, breakwaters, and vessels. In addition, the material of the structure where the sheet-shaped systems 100 are installed is not limited to concrete, and examples of the material further include mortar, metal, glass, resin, tiles, and bricks. Alternatively, the sheet-shaped systems 100 may be installed on a surface of soil or a rock in a construction site, an excavation research site, or the like.

In addition, in some environment where the structure operation support system 10 is installed, energy harvesting may be used to supply power to the loads 140. For example, in a location where light is stably provided, energy harvesting devices such as solar cells may be added to the loads 140 or in the structure operation support system 10 and used as auxiliary power sources. For example, in a location where wind blows stably, wind turbine generators may be added, or in a location where vibrations occur frequently, piezoelectric elements may be added.

The above embodiment and modifications thereof are described as examples for the purpose of describing techniques according to the present invention in detail and is not intended to limit the technical scope of the invention according to the present application to the content of the description. The technical scope of the invention according to the present application includes every possible change, replacement, addition, and omission made by those skilled in the art as conceivable within the range of the specification, drawings, and claims, or within the equivalents thereto.

3. Advantageous Effects

The carbon wires 102 included in the wiring sheets 120 have a high resistance to environment by virtue of the property of hardly corroding of carbon, being a main material thereof. This enables the use of the carbon wires 102 as reliable wirings for a longer term than metals, which are used as materials of wirings in conventional practices. Furthermore, in comparison with copper, which is often used from among metals as a material of wirings, carbon wires are expected to be supplied stably, which brings about a long-term advantage also in terms of initial cost. In addition, being lightweight, capable of resisting repeated bending, good in workability, and good in productivity for unfolding into a large area of carbon wires make it easy to apply carbon wires to a structure having a complex surface shape and a large-scale structure.

In addition, the carbon wires 102 becomes easy to handle and are given a higher endurance when enclosed in insulation sheets 104, which include a material having a high resistance to environment such as polyvinyl chloride resin, so as to be used as wirings capable of being used for a long term.

The wiring sheets 120 having such a high resistance to environment are available for sheet-shaped inspection system (an example of the sheet-shaped system 100) by, for example, being attached such as to connect a plurality of loads 140 including electric circuits with sensors to the carbon wires 102 in combination. Such a sheet-shaped system 100 can be used for a long term even when attached to a surface of a structure in an environment where conventional metal wirings easily deteriorate.

In addition, in a case of a large-scale structure, a large number of sheet-shaped systems 100 may be installed being connected to power source lines, communication lines, and the like that extend all over the structure. This enables implementation of the structure operation support system 10 that allows inspections by simultaneous physical quantity measurements, which is practically impossible by conventional inspections conducted by inspection engineers.

For some object or purpose of measurement, the sensors does not have to operate all the time to collect data, and for example, some data obtained by intermittent measurements, such as performing a measurement in a short time at a predetermined time point of a day, is available to detect an anomaly. In this case, for example, power may be supplied to the loads 140 using carbon wires 102 that have a high resistance but are less expensive, and the loads 140 may charge the power in their power storage elements such as capacitors. Then, electric circuits including the sensors may be operated only at a predetermined time point using the power from these power storage elements, by which processes from measurement to transmission of a measurement result may be performed.

Data on this measurement result is summarized in the centralized control system for the structure and used as an object to be monitored or analyzed. Using the data, for example, it is possible to grasp the status of the entire structure spatially or changes in the status of the entire structure on a time series basis.

In addition, in a case of a structure on which data cannot collected as a whole at a time in conventional practices, using this data brings about a possibility that a status of the structure can be grasped and an anomaly of the structure can be detected in an early stage, by an approach different from conventional one.

In addition, in a location where a high resistance to environment is not required, using the insulation sheet 104 including a material having an electrical insulation property and a flexibility, such as resins other than polyvinyl chloride, cloth, and paper, as a main material, enables a use of the wiring sheet 120 as, for example, a wallpaper that assumes a demanded appearance and provides a high degree of freedom in selecting a spot to take power and signals.

Moreover, contribution to resource conservation and energy saving is expected as an advantageous effects of the present invention.

First, as described above, as a main material, the carbon wires 102 include carbon, a resource that is abundant and is expected to be supplied stably as compared with metals such as copper conventionally used for wirings. Next, the use of the carbon wires 102 realizes a long term endurance longer than ten years, which has often been mentioned as a product life in an electronics field. This reduces an occurrence of repair or replacement, contributing to resource conservation and energy saving.

Furthermore, in a case where the above method employing printing as a production technique for the carbon wires 102, the method contributes to energy saving also in that an amount of heat produced in machining and producing is relatively small.

In addition, using the structure operation support system 10 including the wiring sheets 120 realizes abnormality diagnosis that grasps a structure spatially based on data that cannot be acquired in conventional practices, enabling a useful life of the structure to be prolonged. If this reduces the number of occurrences of building structures, this leads to reduction of emitted $CO_2$ of building materials, construction equipment, and energy consumption and physical distribution. In addition, energy for physical distribution, illumination, and the like necessary for manual inspection operations can be reduced.

In particular, in a large-scale, complex structure such as a service tunnel, resources and energy consumed in construction, inspection, and whole reform are enormous. The structure operation support system 10 according to the present invention is applicable to even such a structure, which brings a great effect of resource conservation and energy saving.

INDUSTRIAL APPLICABILITY

The present invention is available as a wiring sheet, as a sheet-shaped system in which this wiring sheet and a plurality of loads are used in combination, and as a structure operation support system including a plurality of sheet-shaped systems.

The invention claimed is:
1. A wiring sheet, comprising:
one or more carbon wires that are conductors including carbon as a main material and have flexibility, each of the one or more carbon wires being one of a signal line and a power supply line; and
an insulation sheet that encloses an entirety of the one or more carbon wires, includes an electrical insulator as a main material, and has flexibility,
wherein the one or more carbon wires include three or more carbon wires,
the three or more carbon wires include the power supply line, the signal line, and a first ground (GND) line,
in the insulation sheet, the power supply line, the signal line, and the first GND line extend in parallel to each other in a plan view of the insulation sheet, and the signal line is positioned between the power supply line and the first GND line,
the insulation sheet includes:
a plurality of vias each of which extends from a surface of the insulation sheet to a corresponding one of the three or more carbon wires, the plurality of vias not penetrating through the insulation sheet; and
a plurality of external conductors disposed on the surface of the insulation sheet, and
the three or more carbon wires and the plurality of external conductors are electrically connected through the plurality of vias.

2. The wiring sheet according to claim 1,
wherein the main material of the one or more carbon wires is any one of graphene, graphite, and carbon nanotube, and
the main material of the insulation sheet is any one of resin, cloth, and paper.

3. The wiring sheet according to claim 2,
wherein the main material of the insulation sheet is polyvinyl chloride resin.

4. The wiring sheet according to claim 1,
wherein the one or more carbon wires include a carbon wire that has a resistance per centimeter of at least 0.01 ohms and at most 1 ohm.

5. The wiring sheet according to claim 1,
wherein the one or more carbon wires include the power supply line, and
the power supply line forms a grid.

6. The wiring sheet according to claim 1,
wherein the insulation sheet includes a contact that includes anisotropic conductive rubber, is capable of being conductive in a thickness direction of the insulation sheet, and is configured to electrically connect a conductor outside the insulation sheet and the carbon wires.

7. A sheet-shaped system, comprising:
the wiring sheet according to claim 1; and
a plurality of loads that are electrically connected to the one or more carbon wires from an outside of the insulation sheet,
wherein the one or more carbon wires include the power supply line, and
the plurality of loads each include:
   a power storage element configured to receive and store a supply of power from the power supply line; and
   an electric circuit configured to receive a supply of power from the power storage element to operate intermittently.

8. The sheet-shaped system according to claim 7,
wherein the one or more carbon wires include the signal line, and
the electric circuit includes a sensor and is configured to output, via the signal line, a physical quantity measured by the sensor.

9. The sheet-shaped system according to claim 8,
wherein the one or more carbon wires include two or more carbon wires, and
the two or more carbon wires include a second GND line through which no current flows and is used to establish a grounding potential.

10. The sheet-shaped system according to claim 7,
wherein the one or more carbon wires include the power supply line, and
the plurality of loads each include an electric circuit configured to return power stored in the power storage element to the power supply line.

11. The sheet-shaped system according to claim 7,
wherein the one or more carbon wires include the power supply line,
the sheet-shaped system comprising a gateway that electrically connects an electrical wire through which electricity from a power source outside of the sheet-shaped system flows to the power supply line,
wherein the gateway is configured to give instructions on whether to receive a supply of power from the power source via the power supply line, to the plurality of loads.

12. A structure operation support system, comprising:
a plurality of sheet-shaped systems each of which is the sheet-shaped system according to claim 7 that are configured to be installed on a surface of a structure; and
an electrical wire to which the one or more carbon wires included in each of the plurality of sheet-shaped systems are connected.

* * * * *